United States Patent
Tanabe et al.

(10) Patent No.: US 12,165,744 B2
(45) Date of Patent: Dec. 10, 2024

(54) FUNCTIONAL SEQUENCE SELECTION METHOD AND FUNCTIONAL SEQUENCE SELECTION SYSTEM

(71) Applicants: HITACHI, LTD., Tokyo (JP); NATIONAL UNIVERSITY CORPORATION KOBE UNIVERSITY, Kobe (JP); Kyoto University, Kyoto (JP)

(72) Inventors: Maiko Tanabe, Tokyo (JP); Shizu Takeda, Tokyo (JP); Kiyoto Ito, Tokyo (JP); Osamu Imaichi, Tokyo (JP); Kenji Tsuge, Hyogo (JP); Michihiro Araki, Kyoto (JP)

(73) Assignees: Hitachi, Ltd., Tokyo (JP); National University Corporation Kobe University, Kobe (JP); Kyoto University, Kyoto (JP)

( * ) Notice: Subject to any disclaimer, the term of this patent is extended or adjusted under 35 U.S.C. 154(b) by 979 days.

(21) Appl. No.: 16/824,365

(22) Filed: Mar. 19, 2020

(65) Prior Publication Data
US 2020/0327958 A1    Oct. 15, 2020

(30) Foreign Application Priority Data
Mar. 22, 2019   (JP) .................................. 2019-055527

(51) Int. Cl.
*G16B 25/10*        (2019.01)
*G16B 30/00*        (2019.01)
*G16B 35/20*        (2019.01)

(52) U.S. Cl.
CPC ............. *G16B 25/10* (2019.02); *G16B 30/00* (2019.02); *G16B 35/20* (2019.02)

(58) Field of Classification Search
CPC ........ G16B 25/10; G16B 30/00; G16B 35/20; G16B 20/00
See application file for complete search history.

(56) References Cited

U.S. PATENT DOCUMENTS

2007/0218473 A1*   9/2007   Kim ...................... G16B 50/30
                                                                  506/14

OTHER PUBLICATIONS

Bates, M. et al., "Genetic Constructor: An Online DNA Design Platform" ACS Synthetic Biology; vol. 6, Iss. 12; Oct. 11, 2017; pp. 2362-2365.
Nielsen A. A. K. et al., "Genetic circuit design automation" SCIENCE; vol. 352 ISSUE 6281; Apr. 1, 2016 (13 pages).

* cited by examiner

Primary Examiner — Kaitlyn L Minchella
Assistant Examiner — Nidhi Dharithreesan
(74) Attorney, Agent, or Firm — Procopio, Cory, Hargreaves & Savitch LLP

(57) ABSTRACT

A method for making a recombinant gene includes searching a database using a nucleotide sequence of a coding region, a nucleotide sequence that encodes an amino acid sequence, or an amino acid sequence, of a gene, for one or more nucleotide sequences having homology; selecting one or more nucleotide sequences other than nucleotide sequences only derived from a genome from the selected nucleotide sequences; for ones of the selected one or more nucleotide sequences comprising an upstream or downstream nucleotide sequence, analyzing whether the upstream or downstream nucleotide sequence is a functional sequence to select one or more first functional sequences; for ones of the selected one or more nucleotide sequences comprising no upstream or downstream nucleotide sequence, analyzing whether a gene information has any description indicating a functional sequence to select one or more second functional sequences; scoring the selected functional sequences; and selecting one or more functional sequences.

5 Claims, 17 Drawing Sheets
Specification includes a Sequence Listing.

FIG. 8A

| vector name | promoter name | sequence (5–3) | terminator name | sequence (5–3) |
|---|---|---|---|---|
| pBAD TOPO TA | ARA_promoter | CTGACGCTTTTTATCGCAACTCTCTACT | rrnb_terminator | AGAAATTTGCCTGGGGGCCAGTAGCGGTGGTCCCACCTG ACCCCATGCCGAACTCAGAAGTGAAACGCCGTAGCGCCG ATGGTAGTGTGGGGTCTCCCATGCGAGAGTAGGGAACT GCCAGGCATCAAATAAAACGAAAGGCTCAGTCGAAAGAC TGGGCCTTTCGTTT |

| vector name | promoter name | sequence (5'→3') | naturally/artificial | name of terminator | terminator sequence (5'→3') | naturally/artificial | test |
|---|---|---|---|---|---|---|---|
| pBAD TOPO TA | ARA_promoter | CTGACGCTTTTTATCGCAACTCTCTACT | | rrnb_terminator | AGAATTTGGCTGGCGGCAGTAGCGCGGTG GTCCCACCTGACCCCATGCCGAACTCAGA AGTGAAAGGCCGTAGCGCCGATGGTAGTG TGGGGTCTCCCCATGCGAGAGTAGGGAAC TGCCAGGCATCAAATAAAACGAAAGGCTC AGTCGAAAGACTGGGCCTTTCGTTT | A | Add gene |
| pMJ805 | T7_promoter | TAATACGACTCACTATAGGG | A | T7_terminator | ATGCTAGTTATTGCTCAGCGG | A | Snap gene |
| the same hereinafter | .... | .... | .... | .... | .... | .... | .... |

| promoter_seq | | | | |
|---|---|---|---|---|
| promoter_name | promoter_seq | seq_class | reference | score |
| ⦿ ypjDp1 | cgtgcGCGACAAAcgatcGgttaa | A | RegulonDB | 1 |
| ○ ycefp4 | taattTTACCTtttgcataggcgcgcaTATTAActttGtaacg | NA | RegulonDB | 3 |
| ○ yaaAp1 | cggtcGCCAGCTTtctccGgacgc | NA | RegulonDB | 2 |
| ○ - | tagcgTATATACTtcttaAacaat | A | - | - |
| ○ - | gccagGCGaGAGACTgtttcагatt | NA | INFERENCE TOOL | - |
| ○ - | tgtatgCTACGCAgaagttAtcaag | N | INFERENCE TOOL | - |

5'tctaaATGAAGgcgcgactattaccGACGAAGCctcgGcgctgTGAGAATTGGTCACGGCTTCGATGTTCATGCGTTTGGAGGTGAAGGTCCTATAATAATAGGAGGAGTAAGAATTCCCTACGAGAAAGGTCTGTTGGCTCACTCTGATGGCGATGTCGCTTTACATGCGCTAACAGATGCTCTTTTGGGTGCCGCAGCCTTGGGCGACATCGGGAAGTTATTTCCAGATACAGACCCAGCATTCAAGGGAGCTGATAGCAGAGAATTGTTACGTGAAGCATGGCGTCGTATACAAGCAAAAGGTTACACTTTAGGTAACGTAGATGTGACAATTATTGCTCAGGCTCCCAAGATGTTGCCCCATATTCCCCAGATGCGTGTCTTTATTGCCGAGGACTTGGGTTGTCACATGGATGACGTAAACGTGAAGGCTACGACCACTGAAAAATTGGGCTTTACAGGAAGGGGTGAGGGTATCGCTTGTGAAGCAGTGGCCTTGTTGATCAAGGCAACGAAATTAATTGAGTTTGATAATCTCACTTACCTCCACGGTAAACCGCAAGGCACCGGGCTGCTGAAAGCCAATCCGGAAGACTTTGTGGTGGTGGAAGATTTGGGCTTTGAGCCTGATGGTGAAGGTGAGCATATTCTGGTTAGAATCCTCAAAATAAaaaaaaaggatctcaagaagatcctttgatttt3'

FUNCTIONAL SEQUENCE SELECTION METHOD AND FUNCTIONAL SEQUENCE SELECTION SYSTEM

CROSS-REFERENCES

The present application claims the priority to Japanese Patent Application No. 2019-055527 filed on Mar. 22, 2019, which is hereby incorporated by reference.

SEQUENCE LISTING

The instant application contains a Sequence Listing which has been submitted electronically in ASCII format and is hereby incorporated by reference in its entirety. Said ASCII copy, created on Jun. 26, 2020, is named 126042-005UT1_SL.txt and is 10,262 bytes in size.

TECHNICAL FIELD

The present invention relates to functional sequence selection methods and functional sequence selection systems.

BACKGROUND ART

Promoter and terminator sequences, which are functional sequences necessary for introducing a gene into cells and expressing it therein, differ depending on gene sequences to be introduced or species from which the cells are derived; therefore, finding the best sequence needs trial and error. To solve such a problem, required is tools for designing gene sequences which facilitates designing of genes, in particular, selecting the optimum functional sequence. At present, a plurality of such tools has already been developed.

For example, by the search using a name of a gene of interest in databases of National Center for Biotechnology Information (NCBI) and The International Genetically Engineered Machine Competition (iGEM) in the U.S.A., a tool with which registered documents as well as promoter and terminator sequences can be obtained has been developed (see Patent Document 1; Bates M. et al., ACS Synth. Biol., 6, 12 (2017)). This tool allows users to obtain, by choosing documents of interest by themselves from retrieved information, one or more promoter and terminator sequences mentioned in the document(s). With this tool, it is possible to obtain, from the registered documents, functional sequence information suitable for the gene to be introduced; however, researchers are required to read through the document(s) to choose the sequences. Another tool that provides a feature of automatic selection of a functional sequence appropriate for purposes has also been developed (see Patent Document 2; Nielsen A. A. K. et al., Science, 352, 6281 (2016)).

An object of the present invention is to provide novel functional sequence selection methods and functional sequence selection systems.

SUMMARY OF THE INVENTION

The present invention encompasses the following aspects.

An aspect of the present invention is a functional sequence selection method for making a recombinant gene for expressing a gene of interest in a cell using a database containing one or more data elements comprising a sequence of a gene or a part of the gene, an amino acid sequence encoded by a gene or a part of the amino acid sequence and/or a gene information of the gene, the method including the steps of, in a functional sequence selection system including an input device for inputting, as a query, a nucleotide sequence of a coding region of the gene of interest, an amino acid sequence of the gene of interest, or a part thereof; a selection device for selecting a functional sequence; and an output device for outputting the selected functional sequence: inputting a query with the input device; in the selection device, searching the database, with homologous sequence search means, using a nucleotide sequence of a coding region, a nucleotide sequence that encodes an amino acid sequence, or an amino acid sequence, of a gene of interest, for one or more nucleotide sequences having homology to the nucleotide sequence of the coding region of the gene of interest or the nucleotide sequence that encodes the amino acid sequence of the gene of interest; memorizing, with first sequence list memorizing means, the one or more nucleotide sequences obtained by the search as a first sequence list; removing, with functional sequence selecting means, nucleotide sequences only derived from a genome to select one or more nucleotide sequences other than the nucleotide sequences only derived from a genome; (1) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences, and (2) for ones of the selected one or more nucleotide sequences comprising no nucleotide sequence upstream and downstream of a region homologous to the nucleotide sequence or the nucleotide sequence that encodes an amino acid used for the search, analyzing by search whether the gene information in the data element has any description indicating a functional sequence to select one or more second functional sequences; memorizing, with second sequence list memorizing means, a second sequence list comprising the one or more first functional sequences and the one or more second functional sequences; scoring, with scoring means, the first and second functional sequences in the second sequence list; selecting, with functional sequence selection means, one or more functional sequences at high ranks in the scoring result; memorizing, with functional sequence memorizing means, the selected one or more functional sequences at high ranks; and outputting, with the output device, the selected one or more functional sequences at high ranks. The one or more nucleotide sequences other than the nucleotide sequences only derived from a genome may be obtained by analyzing whether the gene information comprises any keyword representing a nucleotide sequence derived from a genome. The functional sequence may include a promoter sequence, a terminator sequence, and a stop codon. In the case of (1), whether the upstream or downstream nucleotide sequence is a functional sequence may be analyzed using a functional sequence library or the gene information. The first and second functional sequences may be scored according to their frequencies of occurrence or according to the frequency of a given keyword in the gene information in the data element to which each functional sequence is relevant. The method may further include the step of removing one or more functional sequences that are naturally occurring in the gene of interest from the first and second functional sequences before scoring the first and second functional sequences.

Another aspect of the present invention is a functional sequence selection system for making a recombinant gene for expressing a gene of interest in a cell using a database containing one or more data elements comprising a sequence of a gene or a part of the gene, an amino acid sequence encoded by a gene or a part of the amino acid sequence and/or a gene information of the gene, the system including: an input device for inputting, as a query, a nucleotide sequence of a coding region of the gene of interest, an amino acid sequence of the gene of interest, or a part thereof; a selection device for selecting a functional sequence, the selection device including: homologous sequence search means for searching the database, using a nucleotide sequence of a coding region, a nucleotide sequence that encodes an amino acid sequence, or an amino acid sequence, of a gene of interest, for one or more nucleotide sequences having homology to the nucleotide sequence of the coding region of the gene of interest or the nucleotide sequence that encodes the amino acid sequence of the gene of interest; first sequence list memorizing means for storing the one or more nucleotide sequences obtained by the search as a first sequence list; functional sequence selecting means for removing nucleotide sequences only derived from a genome to select one or more nucleotide sequences other than the nucleotide sequences only derived from a genome, (1) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences, and (2) for ones of the selected one or more nucleotide sequences comprising no nucleotide sequence upstream and downstream of a region homologous to the nucleotide sequence or the nucleotide sequence that encodes an amino acid used for the search, analyzing by search whether the gene information in the data element has any description indicating a functional sequence to select one or more second functional sequences; second sequence list memorizing means for memorizing a second sequence list comprising the one or more first functional sequences and the one or more second functional sequences; scoring means for scoring the first and second functional sequences in the second sequence list; functional sequence selection means for selecting one or more functional sequences at high ranks in the scoring result; and functional sequence memorizing means for storing the selected one or more functional sequences at high ranks; and an output device for outputting the selected functional sequence. The one or more nucleotide sequences other than the nucleotide sequences only derived from a genome may be selected by analyzing whether the gene information comprises any keyword representing a nucleotide sequence derived from a genome. The functional sequence may include a promoter sequence, a terminator sequence, and a stop codon. In the case of (1), whether the upstream or downstream nucleotide sequence is a functional sequence may be analyzed using a functional sequence library or the gene information. The first and second functional sequences may be scored according to their frequencies of occurrence or according to the frequency of a given keyword in the gene information to which each functional sequence is relevant. The method may further include the step of removing one or more functional sequences that are naturally occurring in the gene of interest from the first and second functional sequences before scoring the first and second functional sequences.

Another aspect of the present invention is a functional sequence selection method for making a recombinant gene for expressing a gene of interest in a cell using a database containing one or more data elements comprising a sequence of a gene or a part of the gene, an amino acid sequence encoded by a gene or a part of the amino acid sequence and/or a gene information of the gene, the method including the steps of: searching the database using a nucleotide sequence of a coding region, a nucleotide sequence that encodes an amino acid sequence, or an amino acid sequence, of a gene of interest, for one or more nucleotide sequences having homology to the nucleotide sequence of the coding region of the gene of interest or the nucleotide sequence that encodes the amino acid sequence of the gene of interest; removing nucleotide sequences only derived from a genome from the one or more nucleotide sequences obtained by the search or the one or more nucleotide sequences that encode the amino acid sequence obtained by the search, to select one or more nucleotide sequences other than the nucleotide sequences only derived from a genome; (1) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences; (2) for ones of the selected one or more nucleotide sequences comprising no nucleotide sequence upstream and downstream of a region homologous to the nucleotide sequence or the nucleotide sequence that encodes an amino acid used for the search, analyzing whether the gene information has any description indicating a functional sequence to select one or more second functional sequences; scoring the first and second functional sequences; and selecting one or more functional sequences at high ranks in the scoring result.

Yet another aspect of the present invention is a program for causing the functional sequence selection system to perform the functional sequence selection method according to any one of the above. Still another aspect of the present invention is a non-transitory computer-readable recording medium in which this program is stored.

INDUSTRIAL APPLICABILITY

The present invention made it possible to provide novel functional sequence selection methods and functional sequence selection systems.

BRIEF DESCRIPTION OF THE DRAWINGS

FIG. 7 discloses SEQ ID NOS 1, 1, and 1, respectively, in order of appearance;

FIG. 8A is a diagram showing a method of selecting a functional sequence region from a patent document shown in FIG. 8A in an embodiment of the present invention. FIG. 8A discloses SEQ ID NOS 3-4, 7-8, 2, and 5, respectively, in order of appearance;

FIG. 8B is an example of a functional sequence library that can be used in an embodiment of the present invention. FIG. 8B discloses SEQ ID NOS 2, 5, 6, and 9, respectively, in order of appearance;

FIG. 10 is a diagrammatic representation showing an interface displaying an output result in an embodiment of the present invention. FIG. 10 discloses SEQ ID NOS 10-12, respectively, in order of appearance;

FIG. 11A discloses SEQ ID NOS 13-16, respectively, in order of appearance;

FIG. 11B shows a pop-up window displaying all promoter sequences on an interface displaying an output result in an embodiment of the present invention. FIG. 11B discloses SEQ ID NOS 13-18, respectively, in order of appearance;

FIG. 12A shows a pop-up window for terminator sequences on an interface displaying an output result in an embodiment of the present invention. FIG. 12A discloses SEQ ID NOS 19-22, respectively, in order of appearance;

FIG. 12B shows a pop-up window displaying all terminator sequences on an interface displaying an output result in an embodiment of the present invention. FIG. 12B discloses SEQ ID NOS 19-23 and 18, respectively, in order of appearance;

FIG. 13 shows a pop-up window for promoter and terminator pairs on an interface displaying an output result in an embodiment of the present invention. FIG. 13 discloses the "promoter" sequences as SEQ ID NOS 13-16 and the "terminator" sequences as SEQ ID NOS 19-22, respectively, in order of appearance;

FIG. 14 discloses SEQ ID NO: 24; and FIG. 15 shows a result of downloaded a sequence on the interface displaying an output result shown in FIG. 10 in an embodiment of the present invention. FIG. 15 discloses SEQ ID NO: 25.

DETAILED DESCRIPTION OF THE INVENTION

Figure 1:
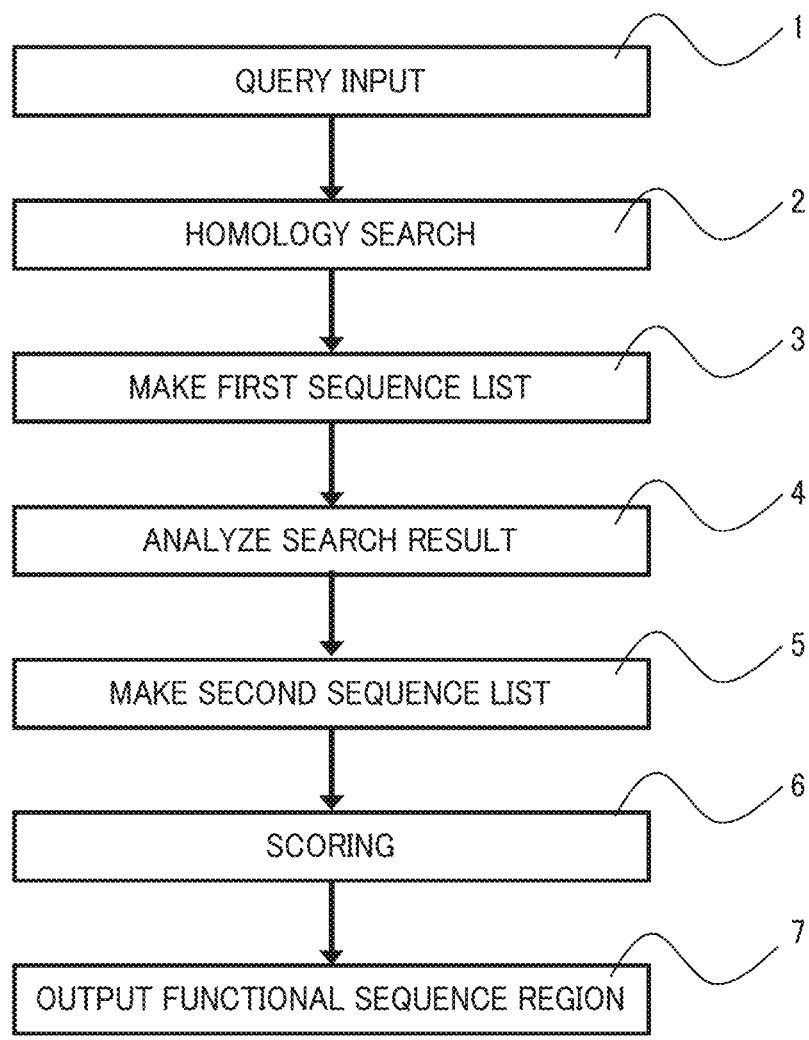
FIG. 1 is a schematic diagram showing steps of a functional sequence selection method according to an embodiment of the present invention.

The objects, features, advantages, and ideas of the present invention are apparent to those skilled in the art from the description of this specification. Those skilled in the art can easily reproduce the present invention from the description herein. The embodiments and specific examples described below represent preferable aspects of the present invention, which are given for the purpose of illustration or explanation. The present invention is not limited thereto. It is obvious to those skilled in the art that various modifications and changes may be made according to the description of the present specification within the spirit and scope of the present invention disclosed herein.

==Functional Sequence Selection Method==

A functional sequence selection method according to an embodiment of the present invention is used. Specifically, a functional sequence selection method for making a recombinant gene for expressing a gene of interest in a cell using a database comprising one or more data elements comprising a sequence of a gene or a part of the gene, an amino acid sequence encoded by a gene or a part of the amino acid sequence and/or a gene information of the gene, the method including the steps of: searching the database using a nucleotide sequence of a coding region, a nucleotide sequence that encodes an amino acid sequence, or an amino acid sequence, of a gene of interest, for one or more nucleotide sequences having homology to the nucleotide sequence of the coding region of the gene of interest or the nucleotide sequence that encodes the amino acid sequence of the gene of interest; removing nucleotide sequences only derived from a genome from the one or more nucleotide sequences obtained by the search or the one or more nucleotide sequences that encode the amino acid sequence obtained by the search, to select one or more nucleotide sequences other than the nucleotide sequences only derived from a genome; (1) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences; (2) for ones of the selected one or more nucleotide sequences comprising no nucleotide sequence upstream and downstream of a region homologous to the nucleotide sequence or the nucleotide sequence that encodes an amino acid used for the search, analyzing whether the gene information comprises any description indicating a functional sequence to select one or more second functional sequences; scoring the first and second functional sequences; and selecting one or more functional sequences at high ranks in the scoring result.

A functional sequence selection method of the present invention is performed in a functional sequence selection system described below. Specifically, a functional sequence selection method for making a recombinant gene for expressing a gene of interest in a cell using a database comprising one or more data elements comprising a sequence of a gene or a part of the gene, an amino acid sequence encoded by a gene or a part of the amino acid sequence and/or a gene information of the gene, the method including the steps of, in a functional sequence selection system including an input device for inputting, as a query, a nucleotide sequence of a coding region of the gene of interest, an amino acid sequence of the gene of interest, or a part thereof; a selection device for selecting a functional sequence; and an output device for outputting the selected functional sequence: inputting a query with the input device; in the selection device, searching the database, with homologous sequence search means, using a nucleotide sequence of a coding region, a nucleotide sequence that encodes an amino acid sequence, or an amino acid sequence, of a gene of interest, for one or more nucleotide sequences having homology to the nucleotide sequence of the coding region of the gene of interest or the nucleotide sequence that encodes the amino acid sequence of the gene of interest; memorizing, with first sequence list memorizing means, the one or more nucleotide sequences obtained by the search as a first sequence list; removing, with functional sequence selecting means, nucleotide sequences only derived from a genome to select one or more nucleotide sequences other than the nucleotide sequences only derived from a genome; (1) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences, and (2) for ones of the selected one or more nucleotide sequences comprising no nucleotide sequence upstream and downstream of a region homologous to the nucleotide sequence or the nucleotide sequence that encodes an amino acid used for the search, analyzing by search whether the gene information in the data element comprises any description indicating a functional sequence to select one or more second functional sequences; memorizing, with second sequence list memorizing means, a second sequence list comprising the one or more first functional sequences and the one or more second functional sequences; scoring, with scoring means, the first and second functional sequences in the second sequence list; selecting, with functional sequence selection means, one or more functional sequences at high ranks in the scoring result; memorizing, with functional sequence memorizing means, the selected one or more functional sequences at high ranks; and outputting, with the output device, the selected one or more functional sequences at high ranks.

The present method is described in detail below.

The method according to this embodiment involves first to seventh steps shown in FIG. 1. Each of these steps is described in detail below.

(First Step)

A first step, i.e., a query input step 1 is a step for starting the method by inputting, as a query, a nucleotide sequence of a coding region of a gene of interest that a user wants to introduce into cells, an amino acid sequence of the gene of interest, or a part thereof. Specifically, the query is a sequence consisting of the following (1) or (2), or a sequence comprising the following (1) or (2):

(1) a nucleotide sequence of a coding region of a gene of interest or a part thereof;

(2) an amino acid sequence encoded by the gene of interest or a part thereof.

When a name of a registered sequence is used, a pre-processing of obtaining a gene sequence from its gene name may be performed and the sequence thus obtained may be inputted as a query. Two or more sequences may be inputted as a query; in such cases, however, it is preferable that they are inputted in a distinguishable manner.

In addition, various parameters and options for a second step (a homology search step 2), a fourth step (a search result analyzing step 4), a sixth step (a scoring step 6), a seventh step (a functional sequence region output step 7) shown in FIG. 1 may also be inputted along with the query.

(Second Step)

The second step, i.e., the homology search step 2 is a step for searching, with the nucleotide sequence of the coding region of the gene of interest, the amino acid sequence of the gene of interest, or the part thereof, which was inputted as the query in the first step and given as a search string, for one or more nucleotide sequences or one or more amino acid sequences with a high similarity to the search string. Such homology searches of nucleotide sequences or amino acid sequences of a gene are performed in one or more biological information database containing sequences of genes and/or their subsequences, amino acid sequences encoded by one of genes and/or their subsequences, and/or gene information.

As examples of the databases that are often used by researchers, Entrez at NCBI, DDBJ at National Institute of Genetics in Japan, European Bioinformatics Institute (EBI) as part of European Molecular Biology Laboratory (EMBL), LocusLink provided by NCBI, and SWISS-PROT mainly with protein information coverage are widely known. The choice which database is used may be determined in advance or specified along with the query in the first step.

Some known methods of homology searches using a database or databases involve the use of Basic Local Alignment Search Tool (BLAST) or SSEARCH, which are tools for finding similarities of nucleotide sequences or amino acid sequences to queries. These tools may be used to obtain information about a gene sequence with a high similarity to the query. Thresholds for reporting homology may be specified along with the query in the first step. As a threshold for reporting homology, the E value may be used in BLAST.

The term "gene information" as used herein refers to a description of features of a gene. The gene information includes, for example, the name and/or ID of a data element for a sequence registered in a database, information about a document in which the sequence is described (e.g., a part or all of the publication date, abstract, author(s), and nucleotide sequences or amino acid sequences and their origins found in the document).

(Third Step)

A third step, i.e., a first sequence list memorizing step 3 is a step for making a list from the information on sequences with high similarities to the search string retrieved in the second step and memorizing the list. The information compiled as a list include one or more nucleotide sequences, amino acid sequences, or nucleotide sequences that encode an amino acid with high similarities to the search string obtained by the search as well as information about the positions of regions with high similarities to the search string on a nucleotide sequence or on an amino acid sequence, the names and/or IDs of data elements for the sequences in the database, and information about documents in which the sequences are found. The information on the positions of regions with high similarities to the search string may be, for example, the number of nucleotides from the 5' end of each registered nucleotide sequence but is not limited thereto.

(Fourth Step)

Figure 2:
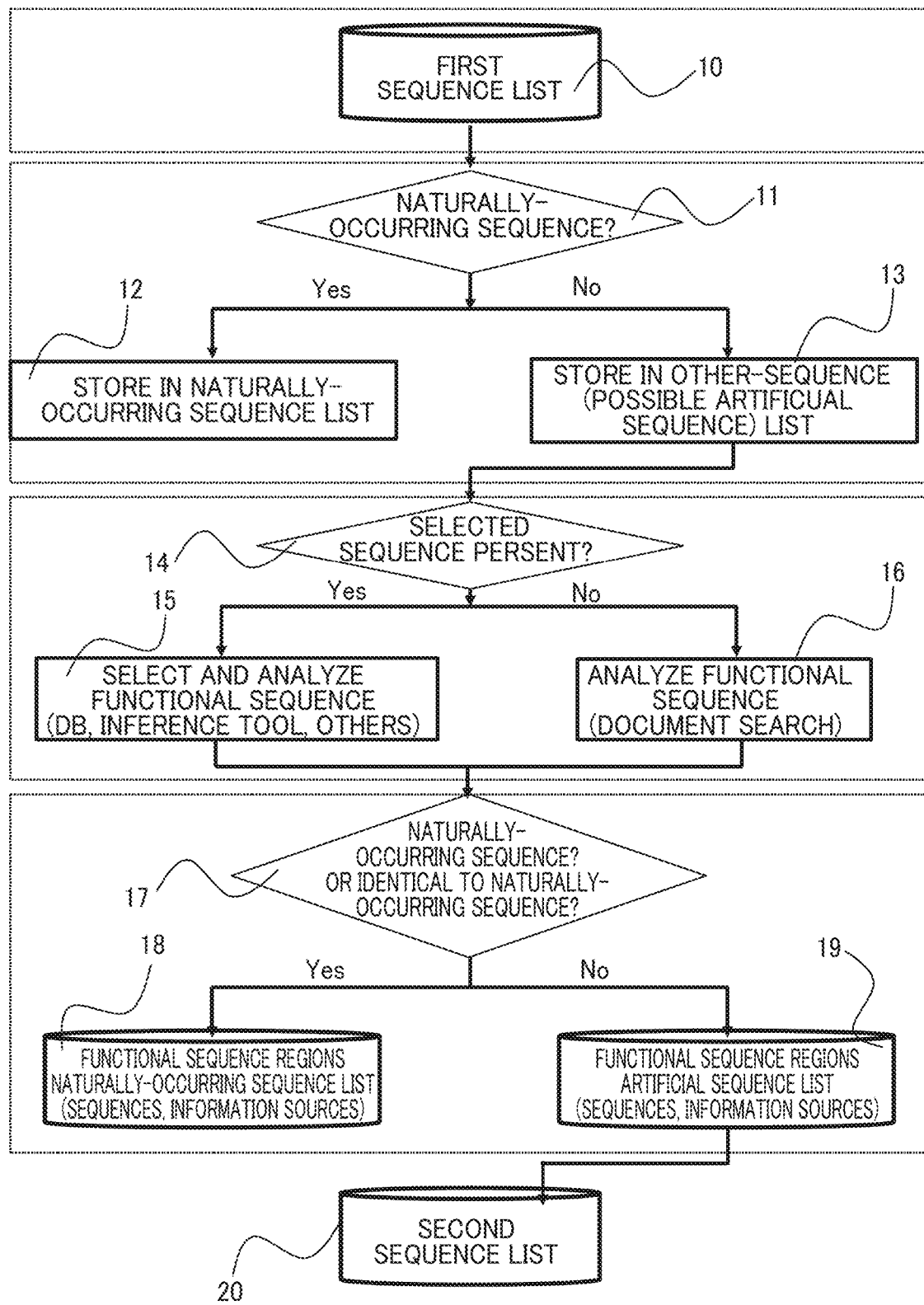
FIG. 2 is a flowchart showing details of third to fifth steps of the functional sequence selection method according to an embodiment of the present invention.

The fourth step, i.e., the search result analyzing step 4 is a step for classifying the nucleotide sequences and their associated information compiled as a list in the third step into a group for naturally-occurring sequences and a group for other sequences (step 4-1), selecting one or more functional sequence regions from the group for other sequences and analyzing them (step 4-2), and then classifying the functional sequence region(s) again into a group for naturally-occurring sequences and a group for artificial sequences (step 4-3). A flowchart of these step is shown in FIG. 2 and is described below.

Step 4-1: Classification into Naturally-Occurring Sequences and Other Sequences

In this step, the data elements for sequences in the first sequence list 10 obtained in the third step are divided into a group for naturally-occurring sequences and a group for other sequences which are candidates of artificial sequences, in a naturally-occurring sequence set-aside step 11. As used herein, the term "naturally-occurring sequence," as shown in step 12, refers to a nucleotide sequence only derived from one or more genomes, that is, a nucleotide sequence consisting of one or more entire genomes or parts of genomes of organisms, whereas the term "artificial sequence" refers to a nucleotide sequence other than the nucleotide sequence only derived from one or more genomes, that is, a nucleotide sequence comprising a sequence that is not naturally occurring. For the classification, naturally-occurring sequences can be identified by, for example, the presence of one or more keywords in the gene information in the data element for a given sequence retrieved during the homology search, the keywords indicating that the sequence in question is naturally occurring. The applicable keywords include, for example, "complete genome," "genome," and "chromosome" but are not limited thereto. The other sequences are those assigned with data elements without any of the above-mentioned keywords. Thus, the data elements other than those for the naturally-occurring sequences can be added to a group for other sequences. Sequences other than the naturally-occurring sequences or sequences assigned with information including one or more keywords indicating that they are artificially designed sequences can be classified as the group for other sequences. The applicable keywords include, for example, "synthesis," "mutant," and their synonyms, but are not limited thereto. It is preferable that the data elements in the first sequence list 10 are classified into a group for naturally-occurring sequences and a group for other sequences in the naturally-occurring sequence set-aside step 11 and then the functional sequence regions are selected and analyzed in the step 4-2; however, the order of the steps is not limited thereto.

Step 4-2: Selecting and Analyzing Functional Sequence Regions

Selecting and analyzing the functional sequence regions is a step of selecting one or more regions having one or more functional sequences required for a gene to function in an organism from the sequences added to the other-sequence list 13 in the step 4-1 and analyzing the functional sequences. The functional sequences include promoter sequences, terminator sequences, and stop codons but are not limited thereto. The term "promoter sequence" as used herein refers to a nucleotide sequence that is required for the initiation of transcription, lies upstream from the transcription initiation site, such as an upstream region of about 300 bp long, 100 bp long, or 60 bp long from the transcription initiation site, and is responsible for the binding of basal transcription factors such as RNA polymerases.

A specific method of analyzing functional sequence regions involves examining whether a nucleotide sequence lies downstream of a region homologous to the nucleotide sequence used for the search or the nucleotide sequence that encodes an amino acid sequence used for the search (a functional sequence region selecting step 14), but different analysis methods are used depending on the results.

In the case that a nucleotide sequence lies upstream or downstream of the region homologous to the nucleotide used for the search or the nucleotide sequence that encodes an amino acid sequence used for the search, a certain length of nucleotide sequence from either end of the coding sequence is selected and is subjected to an analysis to determine whether the selected region have one or more functional sequences, as shown in a functional sequence region selecting and analyzing step 15 in FIG. 2. The term "upstream" and "downstream" as used herein refer to upstream and downstream sides, respectively, immediately adjacent to or away from the region homologous to the query sequence. The upstream region may span upstream from the region homologous to the query sequence, upstream from the start codon, or upstream from the transcription initiation site. The downstream region may span downstream of the region homologous to the query sequence, at a stop codon and downstream therefrom, or downstream of the stop codon. The certain length of the sequence is between 3 bp and 10,000 bp long. The certain length is preferably between 10 and 500 bp long, and more preferably between 20 and 200 bp long. The length of the sequence can be selected independently for the upstream and downstream. The sequences thus selected typically have a promoter sequence on the upstream side and a terminator sequence and/or a stop codon on the downstream side. The methods of analyzing these sequences include those involving: searches for promoter sequences and terminator sequences in one or more functional sequence databases and/or sequences that are commercially used (indicated as "DB" in the functional sequence region selecting and analyzing step 15 in FIG. 2), inferring promoter and terminator sequences using a program for inferring functional sequences (indicated as an inference tool in the functional sequence and analyzing step 15 in FIG. 2), or determining whether the selected sequence has other genetic code sequence(s) and, if any, setting the sequence other than the subject region as a functional sequence (indicated as others in the functional sequence region selecting and analyzing step 15). Known databases used in the method of identifying the functional sequences using DB include, for example, Regulon DB and iGEM. As sequences that are commercially used, pieces of information of products provided by Addgene, Gene Scan, TaKaRa Bio Inc., Thermo Scientific, and Invitrogen can be checked. In this case, a functional sequence library comprising various databases and commercial information can be produced to identify sequences that exactly match or similar to the query. As an identification method using an inference tool, inference using a machine learning approach can be used. Known methods include CNN promoter, Findtermtopic=index&group=programs&subgroup=deep-learn), Findterm. Inference can be made using this technology or a program obtained by modifying this technology. Another method of determining whether the selected sequence has other gene sequence(s) involves searching the selected sequence as a query in the BLAST and/or SSEARCH database(s). A region that encodes the gene sequence is identified by the search, and sequences other than that region can be selected as functional sequence regions. In the case that it is described in a gene information, the information may be used; alternatively, functional sequences may be selected from documents using a text mining technique. The text mining technique is described later.

In the case that no sequence lies upstream and downstream of a region homologous to the nucleotide sequence or the nucleotide sequence that encodes an amino acid sequence which is used for the search, a method of selecting functional sequences from documents using a text mining technique is used, as shown in a functional sequence region analyzing step 16 in FIG. 2. For example, in the case that a gene sequence with a higher similarity to the query is described in a patent document, information about the patent document in question and ID information for the gene sequence found in that document are described in the gene information. Thus, text strings and paragraphs with the ID of that sequence in the entire patent document are scanned to determine whether an associated keyword or keywords are found. If any, by retrieving the keyword(s), information about a promoter or terminator sequence can be obtained. The keywords include "promoter" and "terminator." These words and the nucleotide sequence(s) in the same document can be selected. Other than the keywords just mentioned, the name of a promoter, terminator, vector, or plasmid may be described. In such cases, it is possible to select sequence information by generating a functional sequence library in which the above-mentioned name(s) and the nucleotide sequence information are stored, based on the information about databases and commercial products, as in the searches in DB in the functional sequence region selecting and analyzing step 15.

In this step, it is preferable that a stop codon is also searched for as a functional sequence. The stop codon can be outputted in the sixth step in the case that searches against the three nucleotides at the 5' end of the selected downstream nucleotide sequences provide one or more DNA sequences that are registered as stop codons (TAA, TAG, and TGA), in both of the functional sequence region selecting and analyzing step 15 and the functional sequence region analyzing step 16. In the case that none of these three sequences is present, no stop codon may be presented as the output or the sequence may be presented with TAA being added as the stop codon.

Among the functional sequences, start codons are typically three nucleotides at the 5' end of the nucleotide sequence entered as the query. Thus, it is determined whether the three nucleotides at the 5' end of the query starts from the start codon described below, and if the start codon is found, then it is selected. Eukaryotic nucleotide sequence that encodes start codons is normally ATG but in prokaryotes, GTG and TTG are known in addition to ATG.

Step 4-3: Re-Classification as Naturally-Occurring Sequences and Artificial Sequences A database is generated by combining the selected functional sequences for each of the case where a sequence is found in a region upstream or downstream of a region homologous to query and the case where no sequence is found in the upstream and downstream regions.

As an option for the database, the functional sequence regions selected and analyzed in the step 4-2 and their information can be divided again as follows. A functional sequence region classified as the sequence other than the naturally-occurring sequence can be added to a naturally-occurring sequence list 18 as a naturally-occurring sequence in the case that the subject functional sequence region has the same sequence as one of the sequences classified as the naturally-occurring sequence (a re-classification step 17), and the remaining sequences can be added to an artificial sequence list 19; alternatively, these sequences may be added to a second sequence list 20 without dividing them into two groups.

(Fifth Step)

A fifth step, i.e., a second sequence list memorizing step 5 is for making a second sequence list 20 from the functional sequence region information added to the artificial sequence list 19 obtained in the fourth step, as shown in FIG. 2, and memorizing the second sequence list 20. Information of the data relevant to the first sequence list as well as methods of selecting and analyzing functional sequences can be added to the list along with the sequences. In particular, when functional sequences are identified using a database during the analysis of them, it is preferable that the names of the database and the sequence from which information is obtained are also added to the list.

(Sixth Step)

The sixth step, i.e., the scoring step 6 is for scoring the functional sequences in the second sequence list obtained in the fifth step from a desired perspective. The desired perspective may be, for example, frequency. In this case, the number of each data elements in the second sequence list 20 is used as a score, and the data element that is largest in number is considered as the one at a top rank. A promoter sequence, a terminator sequence, or a sequence pair in that data element is presented. Another desired perspective involves a function required for a functional sequence. For example, when functional sequence information required for a gene to impart a function of synthesizing a certain substance to an organism is examined, functions such as 1. the species to which the gene is to be introduced, 2. whether or not the substance of interest has been synthesized, and 3. the amount of the introduced gene (expression level) in an organism are associated. In such cases, keywords related to the 1, 2, and 3 are given along with the query in the first step, and frequencies of occurrences of these keywords in the information in question are determined in the fourth step, and the numbers of the counts obtained can be presented from the largest as scores. The keywords used as queries may be a keyword other than those for the above-mentioned 1, 2, and 3. In addition, the information against which the keyword searches are made include, for example, the names of data and documents, but are not limited thereto.

(Seventh Step)

The seventh step, i.e., the functional sequence region output step 7 is for selecting one or more functional sequence regions at high ranks based on the scoring performed in the sixth step and outputting them. The functional sequence regions may be outputted as a list. It is desirable that the nucleotide sequences selected here are one or more functional sequences selected from the group of promoter sequences or regions, the gene sequence (including the start codon) used as the query, stop codons, and terminator sequences or regions. The promoter sequence region as used herein refers to a region between a promoter sequence and the start codon, or a region composed of a promoter sequence and an additional sequence added to the promoter sequence on its upstream side. In the case that the additional sequence is predetermined, this sequence may be added to the promoter sequence on its forward or backward end when the promoter sequence is outputted. This condition can be specified along with the query in the first step. For example, in eukaryotes, a Kozak sequence or a TATAbox sequence can be added between the promoter sequence and the start codon. Prokaryotes are also known to have a consensus sequence. An appropriate sequence may be added depending on the species. As in the promoter sequence region, an additional sequence may be added to a terminator sequence region on its forward or backward end. In the case that the additional sequence is predetermined, this sequence may be added to the terminator sequence on its forward or backward end when the terminator sequence is outputted.

==Method of Designing Expression Vectors==

The functional sequences selected by the functional sequence selection method are ligated to the forward and backward ends of the gene of interest and inserted into the appropriate position downstream of the enhancer of an expression vector. As a result, an expression vector with a high expression level of the gene of interest can be produced.

Thus, in constructing expression vectors, it is possible to select functional sequence region information automatically and extensively without limiting gene sequences and species of organisms by selecting sequence information from one or more databases using the functional sequence selection method disclosed herein. Furthermore, in the case that a gene is introduced for a specific purpose, it is possible to select a functional sequence that is the best choice for that purpose by entering the functional sequence information suitable for the purpose beforehand along with a query for scoring, which allows users to automatically obtain the optimum functional sequence information in a short period of time. By constructing an expression vector using an obtained functional sequence, it is possible to construct the best expression vector in introducing a gene.

==Functional Sequence Selection System==

A functional sequence selection system according to this embodiment is for performing the first to seventh steps of the functional sequence selection method. The system includes an input device for inputting, as a query, a nucleotide sequence of a coding region of the gene of interest, an amino acid sequence of the gene of interest, or a part thereof; a selection device for selecting a functional sequence, the selection device including: homologous sequence search means for searching the database, using a nucleotide sequence of a coding region, a nucleotide sequence that encodes an amino acid sequence, or an amino acid sequence, of a gene of interest, for one or more nucleotide sequences having homology to the nucleotide sequence of the coding region of the gene of interest or the nucleotide sequence that encodes the amino acid sequence of the gene of interest; first sequence list memorizing means for storing the one or more nucleotide sequences obtained by the search as a first sequence list; functional sequence selecting means for removing nucleotide sequences only derived from a genome to select one or more nucleotide sequences other than the nucleotide sequences only derived from a genome, (1) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences, and (2) for ones of the selected one or more nucleotide sequences comprising no nucleotide sequence upstream and downstream of a region homologous to the nucleotide sequence or the nucleotide sequence that encodes an amino acid used for the search, analyzing by search whether the gene information in the data element has any description indicating a functional sequence to select one or more second functional sequences; second sequence list memorizing means for memorizing a second sequence list comprising the one or more first functional sequences and the one or more second functional sequences; scoring means for scoring the first and second functional sequences in the second sequence list; functional sequence selection means for selecting one or more functional sequences at high ranks in the scoring result; and functional sequence memorizing means for storing the selected one or more functional sequences at high ranks; and an output device for outputting the selected functional sequence. A specific system is described in detail below.

Figure 3:
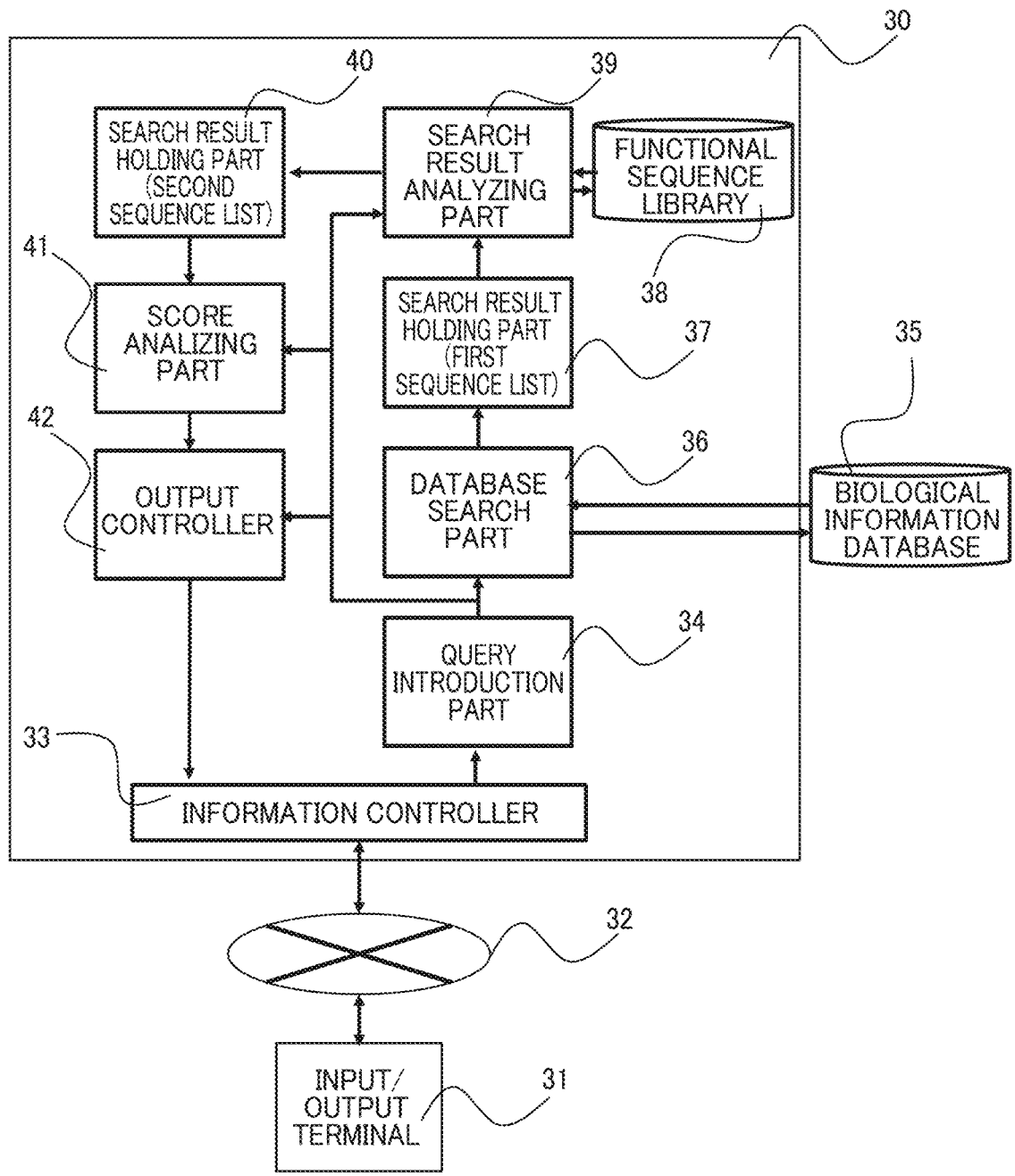
FIG. 3 is a diagrammatic representation of a gene sequence design system according to an embodiment of the present invention.

FIG. 3 shows a block diagram of a gene design system 30 of one embodiment. The functional sequence selection system of this embodiment is composed of an input/output terminal 31 as the input device with which users enter queries; the Internet 32 used for accessing this system; an information controller 33 that serves as the interface as the output device to present queries and output information; a query introduction part 34 that introduces a query into the system; a database search part 36 that performs, as the homologous sequence search means, homology searches with queries using a biological information database 35; a search result holding part 37 that stores homology search results with queries as the first sequence list memorizing means; a functional sequence library 38 and a search result analyzing part 39 used for analyses as the functional sequence selecting means; an analysis result holding part 40 (second sequence list) for holding analysis results as the second sequence list memorizing means; a score analyzing part 41 for scoring, as the scoring means, based on the data in the analysis result holding part 40; and an output controller 42 for selecting output information based on the score analysis results as the functional sequence selection means and the functional sequence memorizing means. The analysis results are displayed by the output controller 42 via the information controller 33.

In the database search part 36, the search result holding part 37, the search result analyzing part 39, the analysis result holding part 40, and the score analyzing part 41, the second step (homology analysis step 2), the third step (the first sequence list making step 3), the fourth step (search result analyzing step 4), the fifth step (second sequence list making step 5), and the sixth step (scoring step 6) in FIG. 1 are successively performed. Details thereof are found in the above-mentioned description of these steps. The functional sequence library means a library in which the names of promoters, terminators, vectors, and plasmids and their sequences are listed and details thereof are found in the description of the step 4-2.

A functional sequence selection method using this system is now briefly described. First, in the functional sequence selection system of this embodiment, the query introduction part 34 receives information about a gene sequence and conditions for search, analysis, scoring, and output entered by a user with the input/output terminal 31. The query introduction part 34 introduces a query and its associated information to the database search part 36, the search result analyzing part 39, the score analyzing part 41, and the output controller 42. The database search part 36 performs homology searches in the biological information database 35 via the query introduction part 34, with the information about a gene sequence and search conditions as search keys and stores the results in the search result holding part 37 as a first sequence list. At that time, the kind of the biological information database 35 and the threshold for reporting homology can be inputted as search conditions. Next, the search result analyzing part 39 classifies the data elements in the search result holding part 37 into a group for naturally-occurring sequences and a group for artificial sequences to select and analyze functional sequence regions using the analysis conditions introduced via the query introduction part 34 as keys, and if necessary, re-classifies the sequences other than the naturally-occurring sequences. The search result analyzing part 39 stores the results thereof in the analysis result holding part 40 as the second sequence list. At that time, the nucleotide length of the selected functional sequence region can be inputted as a parameter for analysis. Furthermore, the database to be referred to during the analyses of the functional sequences can be performed referring to information in the functional sequence library 38. Moreover, the score analyzing part 41 scores the data elements in the analysis result holding part 40 using a scoring method specified via the query introduction part 34 as the key. At that time, the frequency or a keyword related to a desired function can be specified as a scoring method. One or more functional sequences or regions at high ranks obtained here and the gene sequence of the query can be displayed from the output controller 42 via the information controller 33. Here, as an output condition, in the case that there is one or more sequences that the user wants to add to a functional sequence region, the sequence(s) can be used as a query; in such a case, the user can achieve this by entering the condition into the input/output terminal 31.

==Specific Functional Sequence Selection Method==

[1] This embodiment describes an exemplified implementation of the method from the first step to the second sequence list making step which is the fifth step, using the gene design system shown in FIG. 3 that is fundamentally based on the gene design method shown in FIG. 1.

Figure 4:
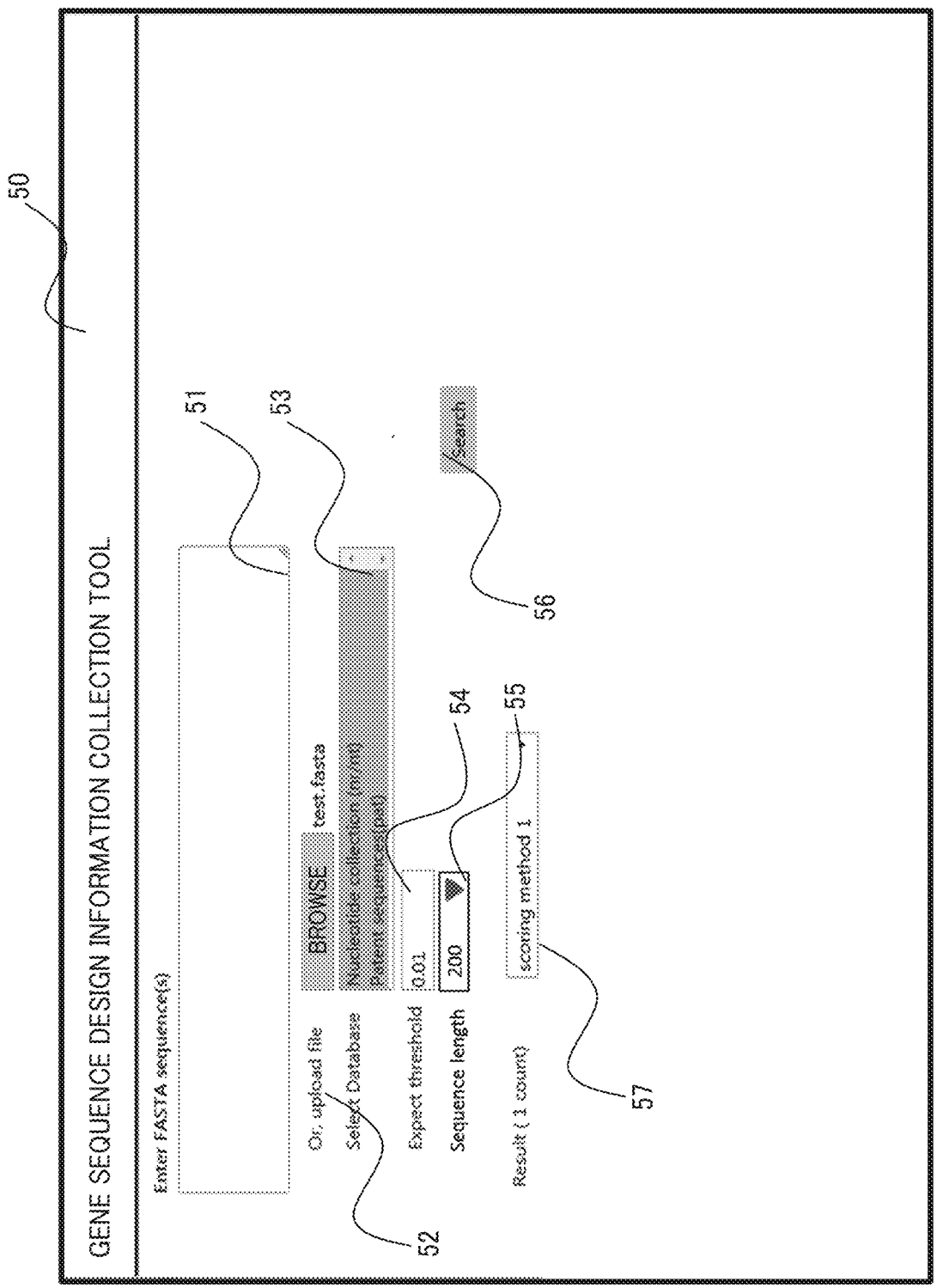
FIG. 4 is a diagrammatic representation of a search interface in an embodiment of the present invention.
Figure 5:
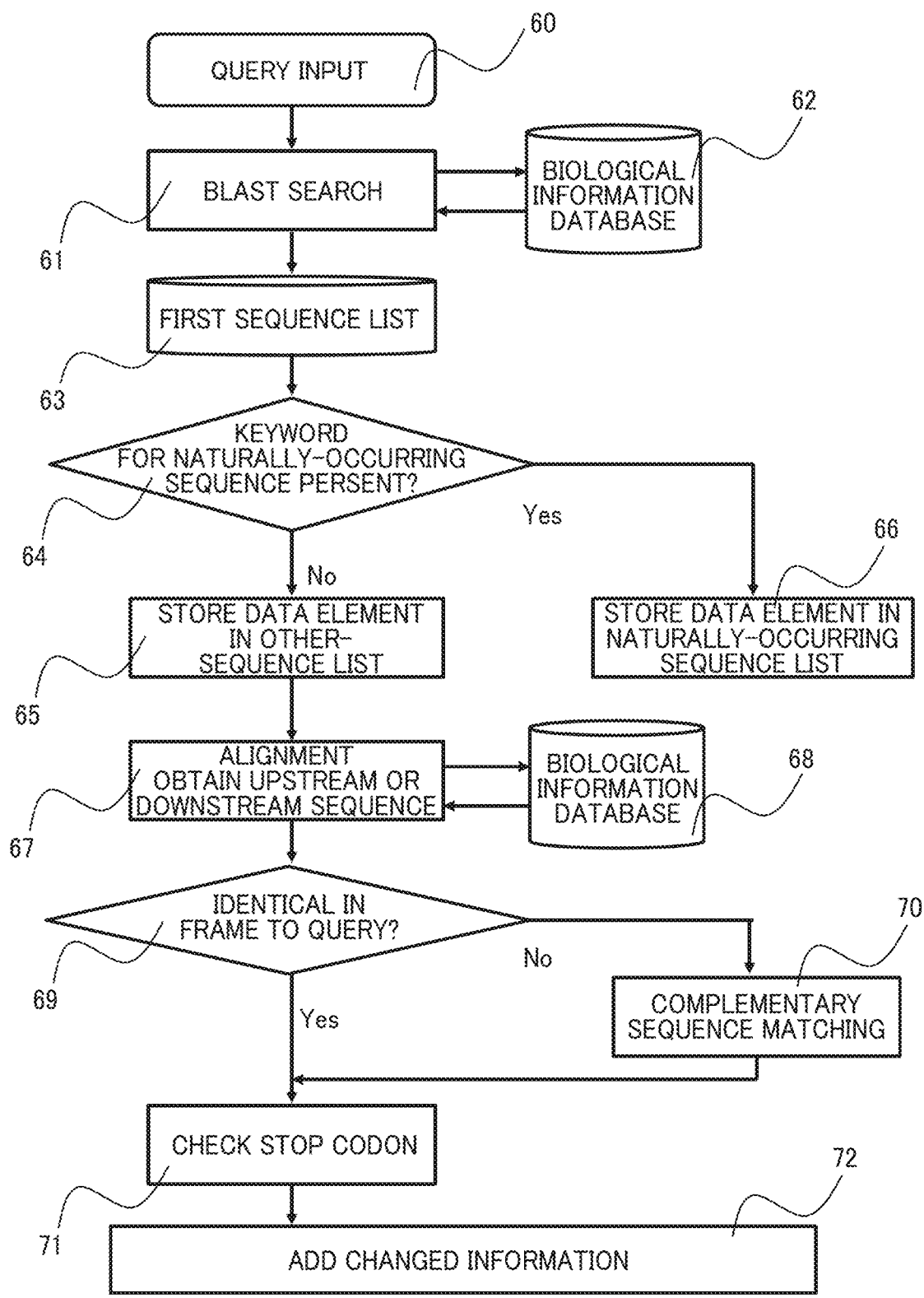
FIG. 5 is a flowchart showing a series of operations from a first step to a step 4-2 in an embodiment of the present invention.
Figure 6:
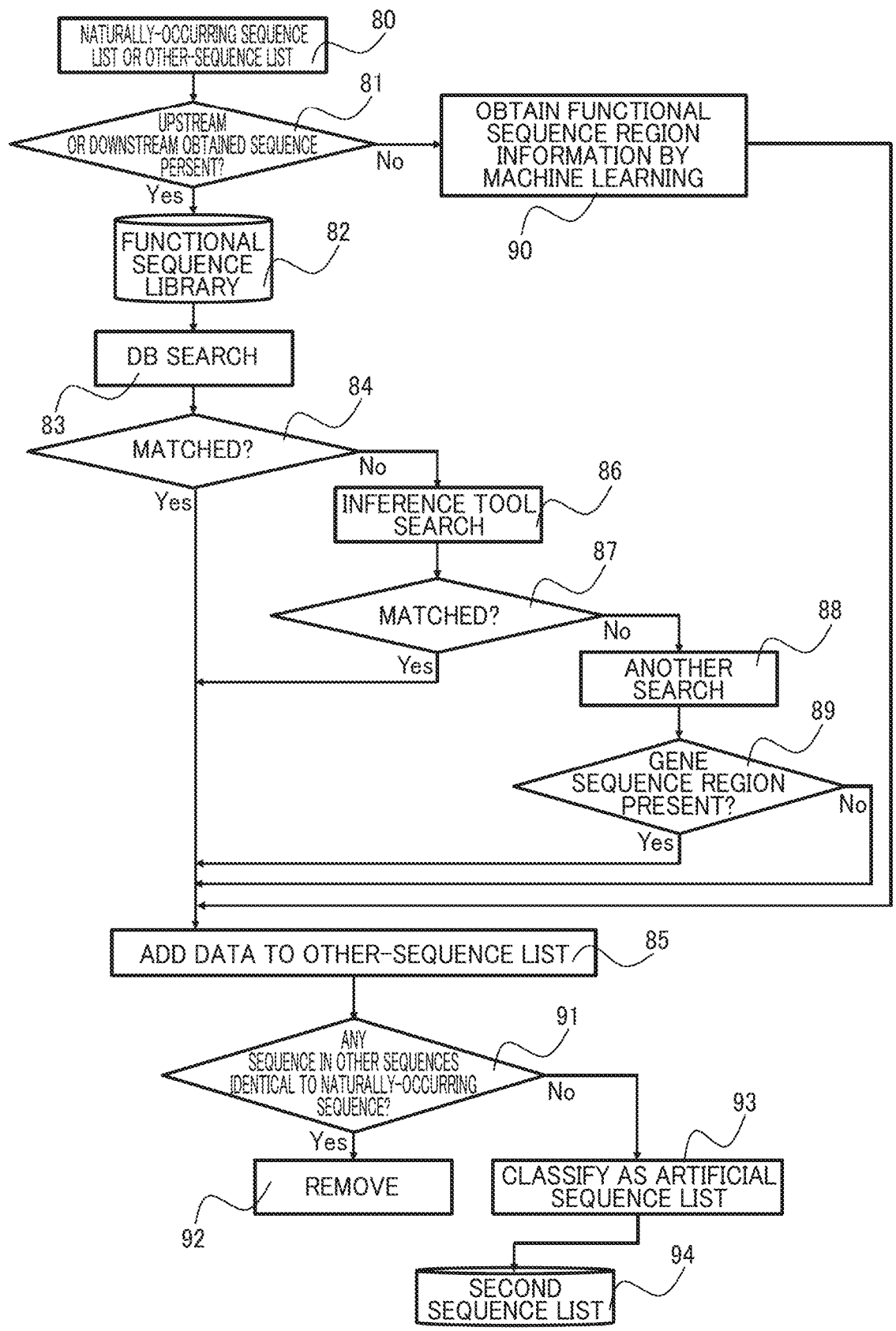
FIG. 6 is a flowchart showing a series of operations from the step 4-2 to a fifth step in an embodiment of the present invention.

Hereinafter, a detailed description is made with reference to FIGS. 4 to 6. FIG. 4 shows a search interface. FIG. 5 shows a flowchart from the first step via the step 4-1 to the functional sequence region selection in the step 4-2, and FIG. 6 shows a flowchart from the functional sequence region analysis in the step 4-2 to the fifth step.

First, a query input step 60 is performed in response to an entry of a query on a search interface 50. A user can directly enter an amino acid sequence of a gene, which is a query of this embodiment, into a gene sequence input area 51 or enter a text file containing the query sequence into an area 52. In addition, since searches are performed in a BLAST search 61 for a homology search step, the user chooses one or more biological information databases 62 and specifies a threshold for reporting homology on the interface as search options for the information associated with the query which are used in this step. In this embodiment, tBLASTn is used for the BLAST search 61. The user chooses the Nucleotide collection of NCBI or a patent sequence database as the biological information databases 62 at a database option field 53 and enters an e-value as a threshold for reporting homology 54. In addition, the user can choose the length of the nucleotide sequence for functional sequence regions used in the step 4-2 in a sequence length option field 55 on the screen. After choosing these options by entering them, the user clicks on a search start button 56 on the interface. In response to this, a homology search starts and the subsequent steps are performed automatically.

The BLAST search 61 is performed and search results are added to a first sequence list 63. Then, a keyword search 64 is performed for the added data elements to determine whether a given data element has "complete genome" or "chromosome" in its data name. Data elements that have the keyword are added to a naturally-occurring sequence list 66 and those that do not have it are added to an other-sequence list 65. In this way, the step 4-1 is performed.

Next, a homology analysis is performed using the other-sequence list 65 in a selecting step 67 to generate alignments between the sequences in the list and the search string and thereby to select sequences upstream and downstream of a region homologous to the nucleotide sequence encoded by an amino acid sequence used as the query. Then, a frame check step 69 is performed to examine whether a frame of each selected sequence lies on the same strand (plus) as the nucleotides coding the amino acid sequence of the query or on the complement strand (minus) using a biological information database 68. Then, the frame information may be added to the first sequence list by referring it. In the case that the frame is on the minus strand, a reverse nucleotide sequence relative to the nucleotide sequence that encodes the amino acid sequence used as the query is displayed in which the orientation of the sequence is inverted relative to the query. Thus, a complementary sequence matching step 70 is performed for the selected sequences. After the positions at which the frames start are made coincide among sequences, it is determined whether the 5' end of the selected downstream sequence has a stop codon (71), and these changes and additional information are added to the other-sequence list (72). In this way, the step 4-2 is performed to select the functional sequence regions.

Subsequently, after the functional sequence regions are selected and stored in an other-sequence list 80, it is determined whether each of the data elements have an upstream or downstream selected sequence (81). Steps with and without an selected sequence are described.

In the case that one or more selected sequences are present, the selected sequences and their information in the database(s) are stored in a functional sequence library 82 and searches are made based on these data (83). In this embodiment, the names of promoters, terminators, vectors, and plasmids and their sequences registered in the RegulonDB, iGEM, and Addgene databases are stored in the functional sequence library 82. Additional data can be entered into this library. For example, the above-mentioned pieces of information provided by Snap Gene, Invitrogen, and Takara Bio Inc., which are commercially used, can be stored. For sequences retrieved in a search result check step 84 for searches in DB 83, change data is added to the other-sequence list (85). Sequences that do not match in the database are then subjected to identification of a functional sequence by searches with an inference tool 86. As this tool, CNNpromoter or Findterm is used. Sequences that do not match in a search result check step 87 for searches with an inference tool 86 are then subjected to identification of a functional sequence by another search 88. For this another search, BLAST is used to determine whether the selected sequence has a region encoded as a gene sequence. In the case that a region homologous to the gene sequence region is found in a search result check step 89 for another search 88, change data is added to the other-sequence list with the sequence region other than the gene sequence region considered as the functional sequence region. In the case that no such a region is found, change data indicative of this is added to the other-sequence list.

In the case that no selected sequence is present, functional sequence region information is selected by a machine learning technique based on the gene information contained in the first sequence list (90). Specifically, using information about documents in which data are described, searches are made with a sequence ID for patent documents and data name for academic documents to select one or more descriptions of the name of a promoter, terminator, vector, or plasmid from texts or sentences where the information in question is described. An example of this is shown in FIG. 7.

Figure 7:
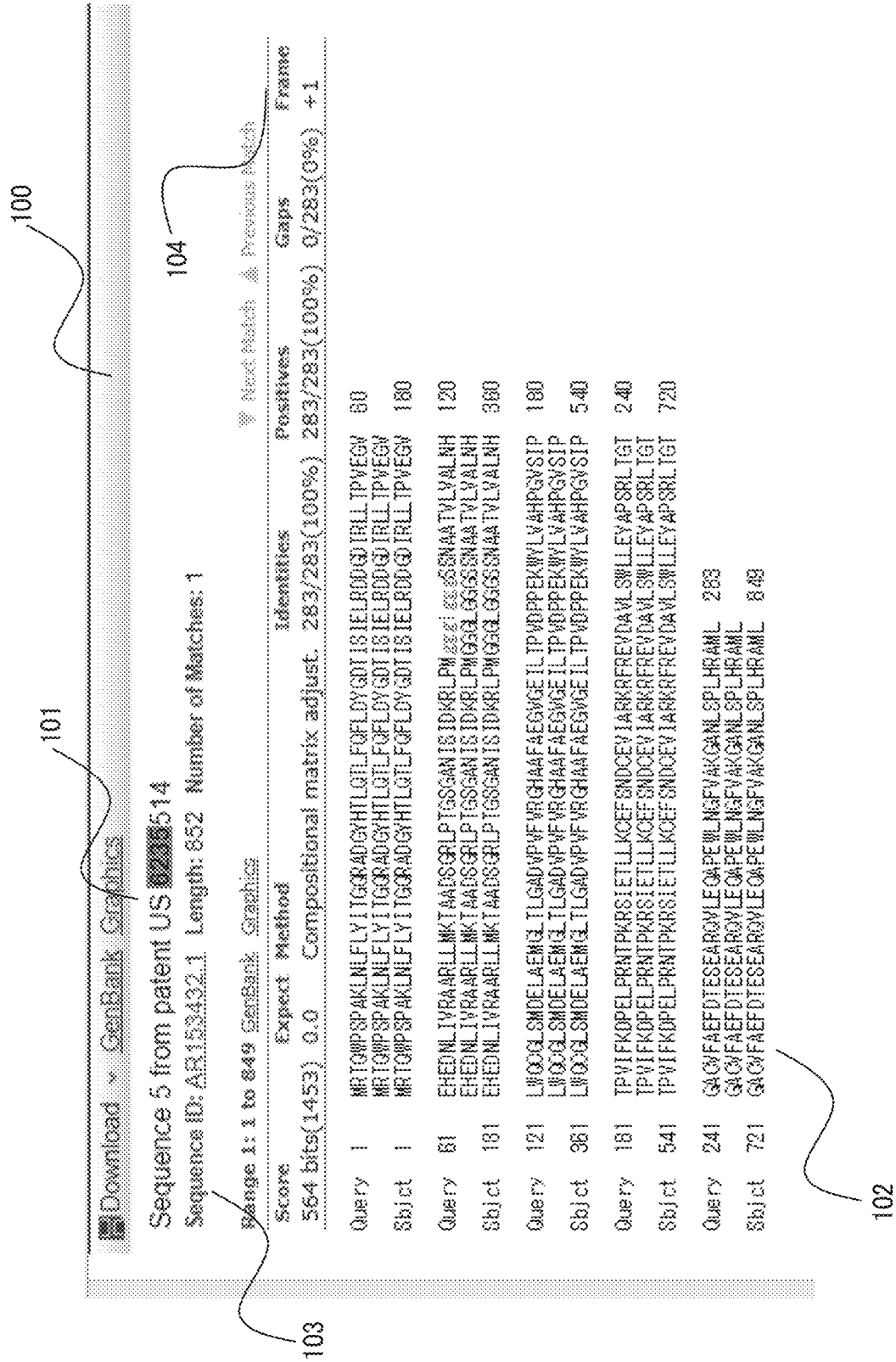
FIG. 7 is an example a result of a homology search showing that there is no nucleotide sequence upstream and downstream of the search string in the step 4-2 in an embodiment of the present invention.

In FIG. 7, sequence information is selected from patent documents using this tool, with an amino acid sequence of ispE gene, which is an enzyme involved in the MEP pathway of E. coli, as a query. First, for example, patent document information 100 as shown in FIG. 7 is selected by the homology search 61 in FIG. 5. Here, a data name with similarity 101, a homologous sequence 102, a database sequence ID 103, and frame information 104 are obtained. These pieces of information are stored in the first sequence list. From the data name 101 and the sequence ID 103 on the database obtained here, the patent document information and information about the sequence IDs found in that patent document are obtained. For the data shown in FIG. 7, the data name 101 indicates the patent document information "U.S. Pat. No. 6,235,514" and the presence of an exact match with the query sequence in the sequence ID (SEQ ID) No: 5 (of U.S. Pat. No. 6,235,514) in the document. The search term used here is "SEQ ID No: 5" (of U.S. Pat. No. 6,235,514). Based on these pieces of information, searches are made for text strings with SEQ ID No: 5 (of U.S. Pat. No. 6,235,514) in the existing patent documents. An image of a search is shown in FIG. 8A. A text string is highlighted by extending forward and backward from the term SEQ ID NO:

5 (of U.S. Pat. No. 6,235,514) in a patent specification 109 and the highlighted area 110 is scanned with keywords contained in the functional sequence library 111. In the case shown in FIG. 8A, the word "pBAD TOPO TA" in the highlighted area 110 is contained in the functional sequence library as a vector name. With this information, a data entry 112 with a promoter name and a terminator name can be obtained. In this way, the functional sequence regions can be selected from the patent document. An example of such functional sequence library 113 is shown in FIG. 8B. The functional sequence library 113 contains a vector name or a plasmid name, the names of a promoter and a terminator and their sequence in that region, information indicating whether these sequences are naturally-occurring or artificial, and data sources. Such libraries are constructed using data selected from the existing databases of promoter, terminator, vector, and plasmid sequences, and from documents describing information about commercially available products. The functional sequence region information thus obtained is added to the other-sequence list as change data (85), as in the case where an selected sequence is found. The analysis of the functional sequence region in the step 4-2 is performed by this step.

Next, using a genome database or the like, it is determined in a search result check step 91 where functional sequence and region identical to those in the naturally-occurring sequence list are found in the other-sequence list. If any, they are removed from the other-sequence list (92); if not, the contents of the other-sequence list are classified as an artificial sequence list (93). The obtained artificial sequence list is stored as a second sequence list 94. As apparent from the above, by entering an amino acid sequence of a gene that a user wants to introduce as a query, it is possible to obtain functional sequence regions used upon the gene introduction as the second sequence list.

[2] This embodiment describes an exemplified implementation of the method from the fifth step to the seventh step, using the gene design system shown in FIG. 3 that is fundamentally based on the gene design method shown in FIG. 1.

Figure 9:
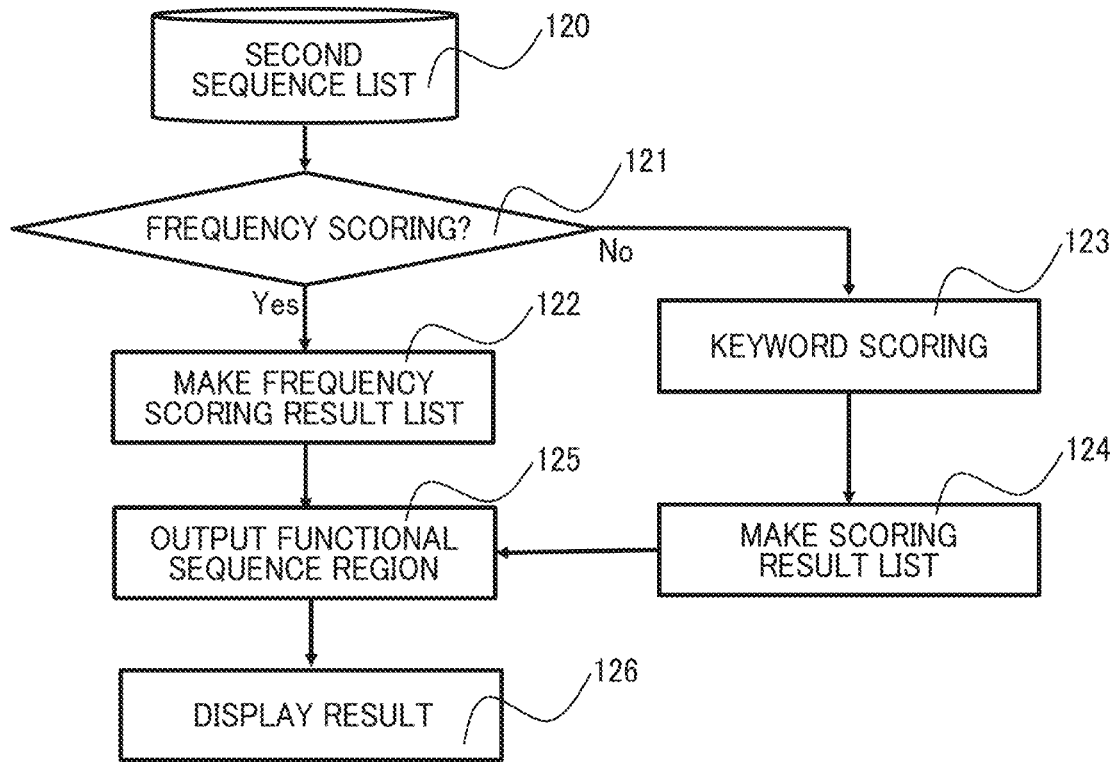
FIG. 9 is a flowchart showing the fifth step to a seventh step in an embodiment of the present invention.
Figure 10:
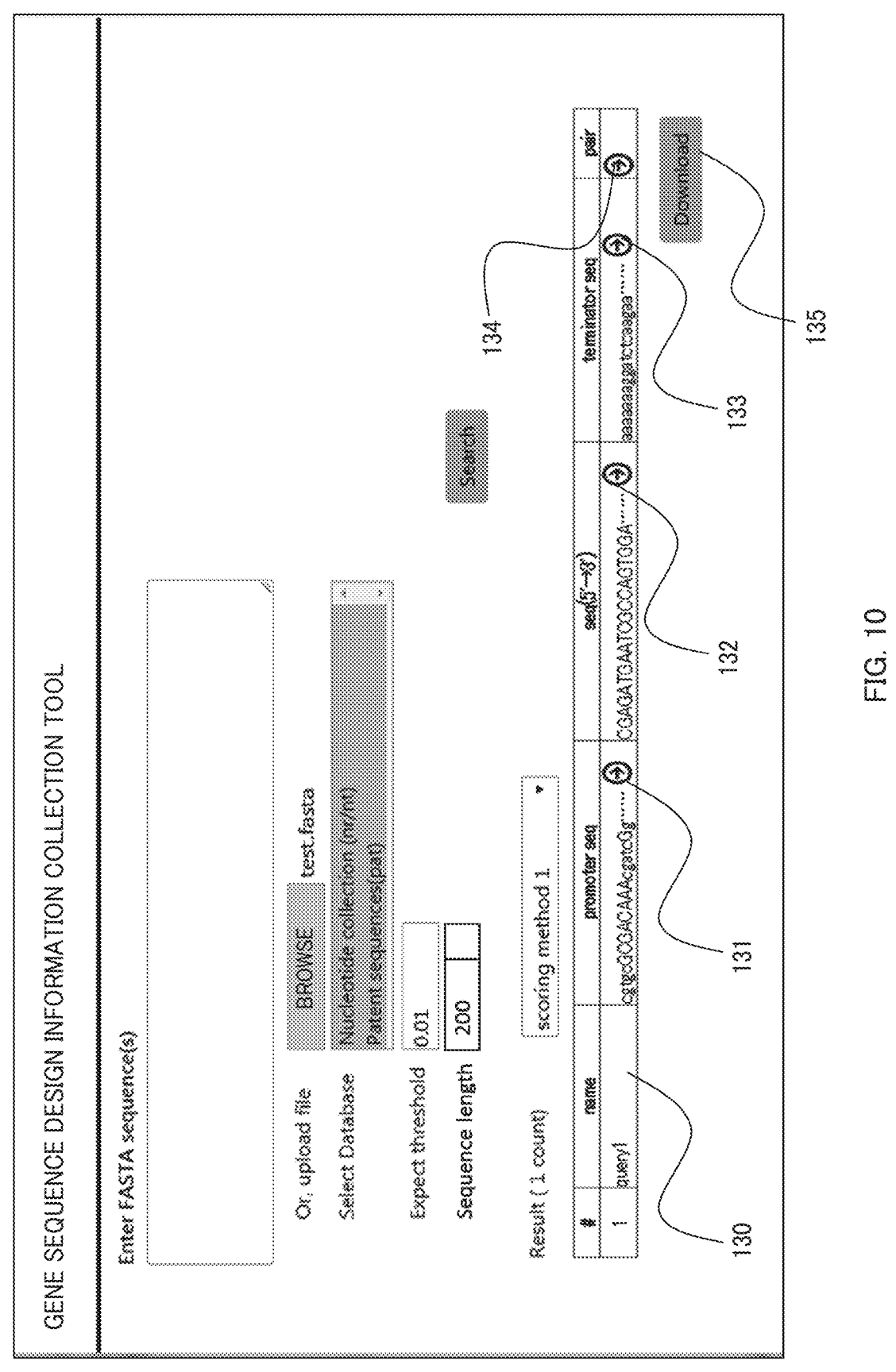

FIG. 9 is a flowchart showing the fifth step, the scoring step of the sixth step, and the functional sequence region output step of the seventh step. FIG. 10 shows an output result display interface. The scoring method is chosen, in entering a query in the first step, on which is used, frequency or a keyword under desired conditions. This choice can be made with the option 57 for the scoring method on the search interface shown in FIG. 4.

In the case that scoring by frequency is chosen in a scoring method choosing step 121 in FIG. 9, frequency scoring is carried out for the information on the number of the registered elements in a second sequence list 120. The results are stored in a frequency scoring result list (122). In the case that frequency scoring is not chosen, the percentage of appearance of a desired scoring keyword is used for the scoring. The keyword for this scoring can be entered with the option 57 for the scoring method in FIG. 4. In a keyword scoring step 123, the documents or data names in the gene information are searched on whether this keyword entered here is present and the number of the keywords is counted as a score. Based on this score, a keyword score result list is made (124). Regardless of which scoring method is used, elements at high ranks in the obtained results are outputted. The functional sequences, i.e., the nucleotide sequences of the gene sequence entered as the query, including the promoter, terminator, stop codon, and/or start codon, are selected as output data in a functional sequence region output step 125, and the results are displayed on an interface shown in FIG. 10 (126). FIG. 10 shows an example of a representation of an output result 130 for the elements at higher ranks at the bottom of the search interface. A promoter sequence, a nucleotide sequence of a gene, a terminator sequence, and a promoter-terminator pair sequence are displayed. By clicking pop-up buttons 131, 132, 133, and 134 for the respective display areas, pop-up windows for them are displayed as shown in FIGS. 11, 12, 13, and 14.

Figure 11A:
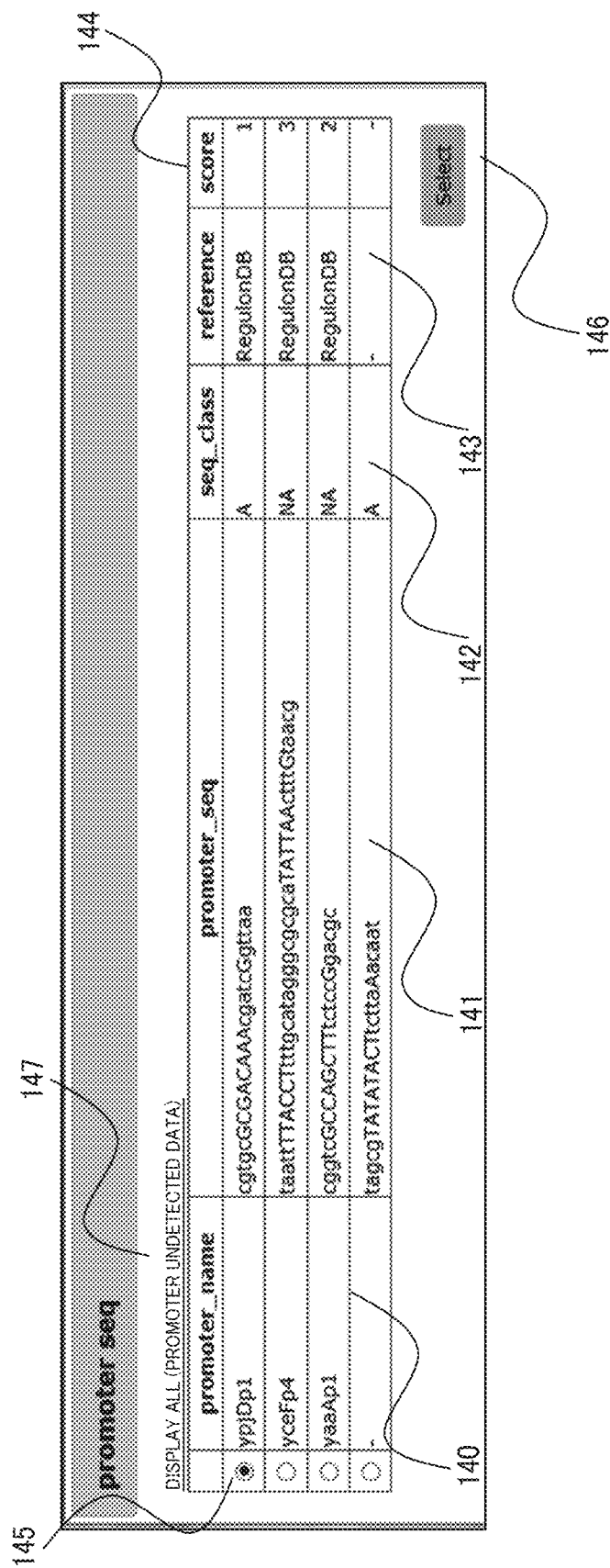
FIG. 11A shows a pop-up window for promoter sequences on an interface displaying an output result in an embodiment of the present invention.
Figures 12A, 12B:
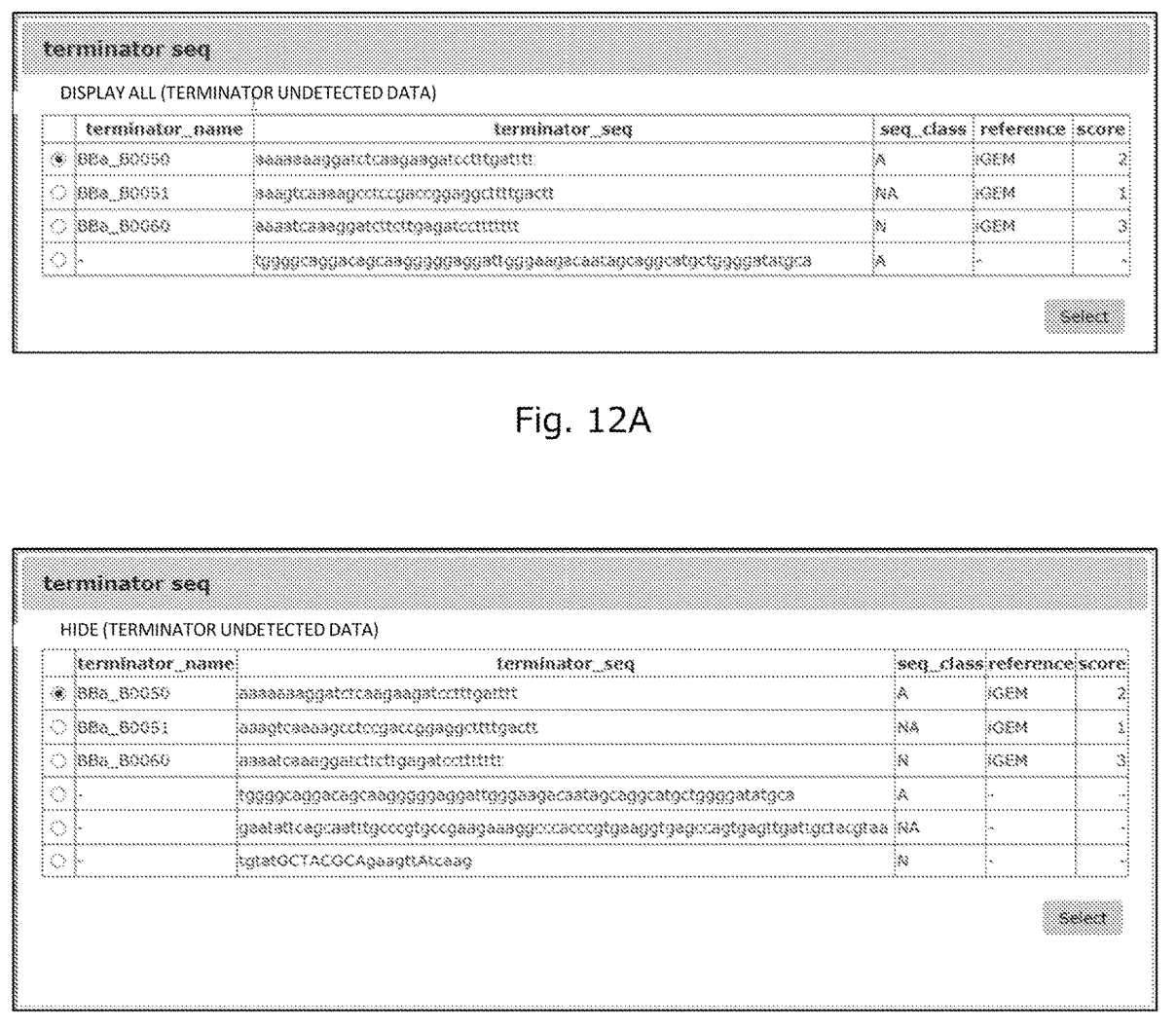
Figure 13:
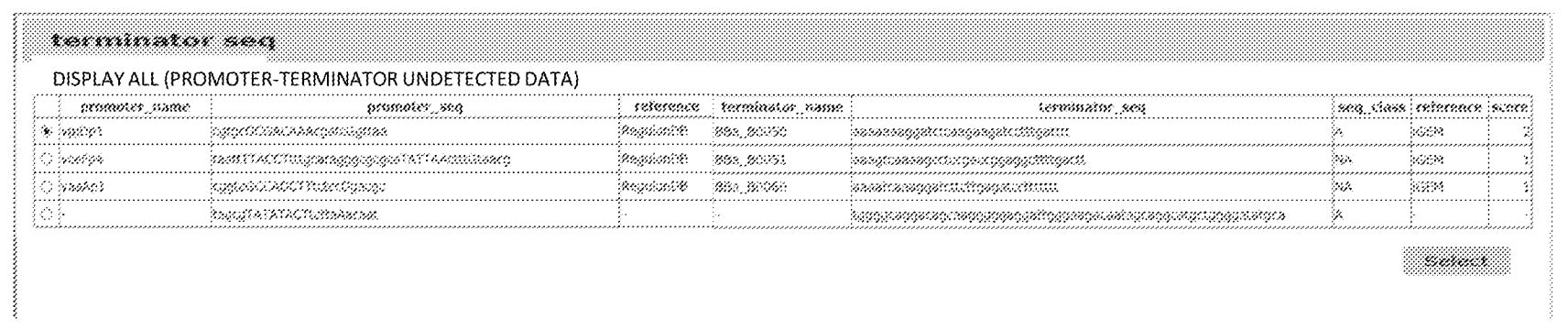
Figure 14:
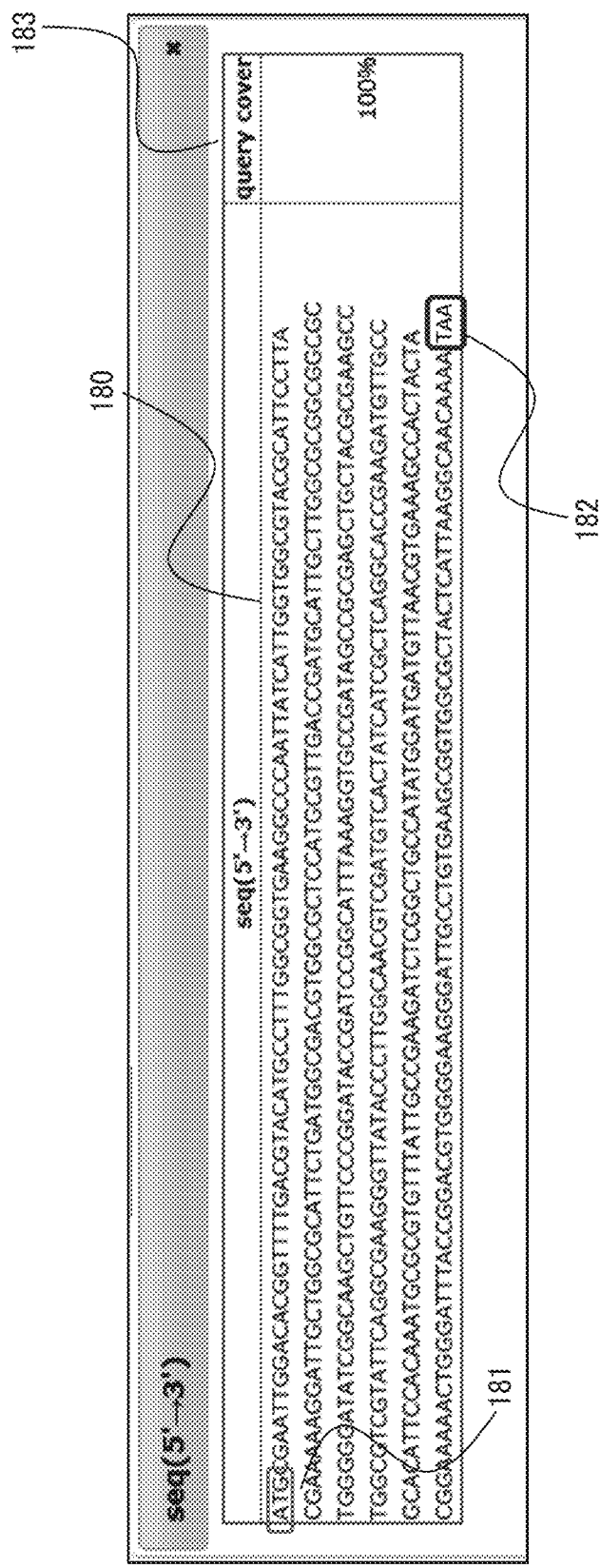
FIG. 14 shows a pop-up window for a nucleotide sequence used as a query on an interface displaying an output result in an embodiment of the present invention.

First, when the pop-up button 131 is clicked for the promoter sequence, as shown in FIG. 11A, promoter names 140 and promoter region sequences 141 which are obtained upon the identification with the specified condition; discriminators 142 indicating which class of a naturally-occurring sequence (denoted by "N" in the figure), an artificial sequence (denoted by "A" in the figure), or both (denoted as "N/A" in the figure) each sequence belongs to, sequence identification methods and database information 143 used for the identification, and the frequency scores 144 are shown. As the sequence identification methods, there are a DB method referring to a functional sequence library, a method using an inference tool, and other methods. In the case that regions are identified with the DB method, the database name in the functional sequence library is displayed. In the case that the regions are inferred with the inference tool method or other method, the inference tool or others (indicated by a hyphen in the figure) is displayed. Then, the artificial sequence with the highest score is displayed at the top of the scoring list. It is also possible to change the arrangement of the results displayed in FIG. 10 by clicking on a check box 145 in FIG. 11 and clicking a select button 146. Furthermore, by clicking a display-all button 147, all the results obtained by the searches can be displayed (display all results 148) as shown in FIG. 11B. This operation is also possible to pop-up windows for the terminator sequences shown in FIG. 12 and for the promoter-terminator sequence pairs shown in FIG. 13. Moreover, FIG. 14 shows a pop-up window for a nucleotide sequence 170 of the gene entered as the query for this analysis, with the start codon 171 at the 5' end and a stop codon 172 at the 3' end. A query coverage 173 is also displayed, and the nucleotide sequence with the query coverage of 100% is displayed in FIG. 10 and this pop-up window. In this way, for each sequence, sequences at high ranks or arbitrarily selected sequences are displayed in FIG. 10, and by clicking a download button 135, a gene sequence having a promoter sequence 181, the start codon 182, and a stop codon 183, and a terminator sequence 184 can be displayed at once, as shown in an output sequence 180 in FIG. 14. With the second sequence list 190 in which the functional sequence region(s) for an amino acid sequence of a gene that a user wants to introduce into cells, the promoter 191 and/or terminator sequence(s) 194 which are functional sequences can be identified or inferred, and optimum functional sequence information can be obtained automatically by scoring with a desired condition. As described above, this tool makes it possible to reduce the time required for designing gene sequences.

==Program and Computer-Readable Recording Medium==

An embodiment of the present invention is a program for causing the above-mentioned functional sequence selection system to perform the above-mentioned functional sequence selection method. In addition, a recording medium in which this program is stored in a computer-readable manner is also an embodiment of the present invention. With them, the above-mentioned functional sequence selection method can be made widely available and versatile.

EXAMPLES

Hereinafter, the present invention is described more specifically based on examples, but the present invention is not limited thereto. Those skilled in the art can change the present invention to various embodiments without departing from the spirit of the present invention, and these changes are also encompassed in the scope of the present invention.

The examples below show that functional sequences were obtained through the steps shown in FIG. 6 with a specified query.

Example 1

Database searches (83) in FIG. 6 made with the following conditions provided RegulonDB: ispFp2 as a promoter and (iGEM:BBa_B0010) as a terminator.

Amino acid sequence of a gene, which is one of the queries: gene of non-mevalonate pathway, ispF Biological information database: choose databases for nucleotide collection and patent sequences Length of upstream and downstream obtained sequences: 1000 bp

Example 2

Database searches (83) in FIG. 6 made with the following conditions provided no functional sequence. Accordingly, blast searches (88) were made. Then, a gene coding region "hypothetical protein AC239_22870" was detected at positions 196 to 804 nt from the 5' end of an upstream selected nucleotide sequence (1000 nt) and a lac promoter sequence was detected in the remaining sequence of 196 nt.

Amino acid sequence of a gene, which is one of the queries: gene of non-mevalonate pathway, ispG Biological information database 62: choose databases for nucleotide collection and patent sequences Length of upstream and downstream selected sequences: 1000 bp.

---

The invention claimed is:

1. A functional sequence selection method for making a recombinant gene for expressing a gene of interest in a cell using a database comprising one or more data elements comprising a sequence of a gene or a part of the gene, an amino acid sequence encoded by a gene or a part of the amino acid sequence and/or a gene information of the gene, the method comprising:

searching the database using a nucleotide sequence of a coding region or a nucleotide sequence that encodes an amino acid sequence of a gene of interest, for one or more nucleotide sequences having homology to the nucleotide sequence of the coding region of the gene of interest or the nucleotide sequence that encodes the amino acid sequence of the gene of interest;

removing nucleotide sequences only derived from a genome from the one or more nucleotide sequences obtained by the search, to select one or more nucleotide sequences other than the nucleotide sequences only derived from a genome;

(a) for ones of the selected one or more nucleotide sequences comprising a nucleotide sequence upstream or downstream of a region homologous to the nucleotide sequence or the nucleotide sequence that encodes an amino acid used for the search, analyzing whether the upstream or downstream nucleotide sequence is a functional sequence to select one or more first functional sequences;

(b) for ones of the selected one or more nucleotide sequences comprising no nucleotide sequence upstream and downstream of a region homologous to the nucleotide sequence or the nucleotide sequence that encodes an amino acid used for the search, analyzing whether the gene information comprises any description indicating a functional sequence to select one or more second functional sequences;

scoring the first and second functional sequences based on:
   frequencies of occurrence of the first and second functional sequences; or frequency of a given keyword in the gene information;
selecting one or more functional sequences at specific ranks in the scoring result; and
constructing an expression vector using the selected one or more functional sequences to reduce a time required for designing gene sequences.

2. The functional sequence selection method according to claim 1, wherein the one or more nucleotide sequences other than the nucleotide sequences only derived from a genome are selected by analyzing whether the gene information comprises any keyword representing a nucleotide sequence derived from a genome.

3. The functional sequence selection method according to claim 1, wherein the first and second functional sequences comprise a promoter sequence, a terminator sequence, or a stop codon.

4. The functional sequence selection method according to claim 1, wherein, in a case of (a), whether the upstream or downstream nucleotide sequence is a functional sequence is analyzed using a functional sequence library or the gene information.

5. The functional sequence selection method according to claim 1, further comprising removing one or more functional sequences that are naturally occurring in the gene of interest from the first and second functional sequences before scoring the first and second functional sequences.

* * * * *

SEQUENCE LISTING

<160> NUMBER OF SEQ ID NOS: 25

<210> SEQ ID NO 1
<211> LENGTH: 283
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Met Arg Thr Gln Trp Pro Ser Pro Ala Lys Leu Asn Leu Phe Leu Tyr
1               5                   10                  15

Ile Thr Gly Gly Arg Ala Asp Gly Tyr His Thr Leu Gln Thr Leu Phe
            20                  25                  30

Gln Phe Leu Asp Tyr Gly Asp Thr Ile Ser Ile Glu Leu Arg Asp Asp
        35                  40                  45

Gly Asp Leu Arg Leu Leu Thr Pro Val Glu Gly Val Glu His Glu Asp
    50                  55                  60

Asn Leu Ile Val Arg Ala Ala Arg Leu Leu Met Lys Thr Ala Ala Asp
65                  70                  75                  80

Ser Gly Arg Leu Pro Thr Gly Ser Gly Ala Asn Ile Ser Ile Asp Lys
                85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Met
        115                 120                 125

Asp Glu Leu Ala Glu Met Gly Leu Thr Leu Gly Ala Asp Val Pro Val
    130                 135                 140

Phe Val Arg Gly His Ala Ala Phe Ala Glu Gly Val Gly Glu Ile Leu
145                 150                 155                 160

Thr Pro Val Asp Pro Pro Glu Lys Trp Tyr Leu Val Ala His Pro Gly
                165                 170                 175

Val Ser Ile Pro Thr Pro Val Ile Phe Lys Asp Pro Glu Leu Pro Arg
            180                 185                 190

Asn Thr Pro Lys Arg Ser Ile Glu Thr Leu Leu Lys Cys Glu Phe Ser
        195                 200                 205
```

```
Asn Asp Cys Glu Val Ile Ala Arg Lys Arg Phe Arg Glu Val Asp Ala
    210                 215                 220
Val Leu Ser Trp Leu Leu Glu Tyr Ala Pro Ser Arg Leu Thr Gly Thr
225                 230                 235                 240
Gly Ala Cys Val Phe Ala Glu Phe Asp Thr Glu Ser Glu Ala Arg Gln
                245                 250                 255
Val Leu Glu Gln Ala Pro Glu Trp Leu Asn Gly Phe Val Ala Lys Gly
            260                 265                 270
Ala Asn Leu Ser Pro Leu His Arg Ala Met Leu
            275                 280

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctgacgcttt ttatcgcaac tctctact                                        28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atggcttcct cctcccattt cctc                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ttcagcatcc tgaggaaaag acgg                                            24

<210> SEQ ID NO 5
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
agaatttgcc tggcggcagt agcgcggtgg tcccacctga ccccatgccg aactcagaag      60
tgaaacgccg tagcgccgat ggtagtgtgg ggtctcccca tgcgagagta gggaactgcc     120
aggcatcaaa taaaacgaaa ggctcagtcg aaagactggg cctttcgttt               170

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 6
taatacgact cactataggg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atgcggacac agtggccctc                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagcatggct ctgtgcaatg                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgctagtta ttgctcagcg g                                             21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cgtgcgcgac aaacgatcgg                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgagatgaat cgccagtgga                                               20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 12
aaaaaaagga tctcaagaa                                                    19

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgtgcgcgac aaacgatcgg ttaa                                              24

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
taattttacc ttttgcatag ggcgcgcata ttaactttgt aacg                        44

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cggtcgccag ctttctccgg acgc                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tagcgtatat acttcttaaa caat                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gccaggcgag actgtttcgg attt                                              24

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
```
tgtatgctac gcagaagtta tcaag                                              25

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaaaaaagga tctcaagaag atcctttgat ttt                                     33

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aaagtcaaaa gcctccgacc ggaggctttt gactt                                   35

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaatcaaag gatcttcttg agatcctttt ttt                                     33

<210> SEQ ID NO 22
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
tggggcagga cagcaagggg gaggattggg aagacaatag caggcatgct ggggatatgc        60
a                                                                        61

<210> SEQ ID NO 23
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gaatattcag caatttgccc gtgccgaaga aaggcccacc cgtgaaggtg agccagtgag        60
ttgattgcta cgtaa                                                         75

<210> SEQ ID NO 24
<211> LENGTH: 480
<212> TYPE: DNA
<213> ORGANISM: Artificial Sequence
<220> FEATURE:
<223> OTHER INFORMATION: Description of Artificial Sequence: Synthetic

```
           polynucleotide

<400> SEQUENCE: 24
atgcgaattg gacacggttt tgacgtacat gcctttggcg gtgaaggccc aattatcatt    60
ggtggcgtac gcattcctta cgaaaaagga ttgctggcgc attctgatgg cgacgtggcg   120
ctccatgcgt tgaccgatgc attgcttggc gcggcggcgc tgggggatat cggcaagctg   180
ttcccggata ccgatccggc atttaaaggt gccgatagcc gcgagctgct acgcgaagcc   240
tggcgtcgta ttcaggcgaa gggttatacc cttggcaacg tcgatgtcac tatcatcgct   300
caggcaccga agatgttgcc gcacattcca caaatgcgcg tgtttattgc cgaagatctc   360
ggctgccata tggatgatgt taacgtgaaa gccactacta cggaaaaact gggatttacc   420
ggacgtgggg aagggattgc ctgtgaagcg gtggcgctac tcattaaggc aacaaaataa   480

<210> SEQ ID NO 25
<211> LENGTH: 706
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tctaaatgaa ggcgcgacta ttaccgacga agcctcggcg ctgtgagaat tggtcacggc    60
ttcgatgttc atgcgtttgg aggtgaaggt cctataataa taggaggagt aagaattccc   120
tacgagaaag gtctgttggc tcactctgat ggcgatgtcg ctttacatgc gctaacagat   180
gctcttttgg gtgccgcagc cttgggcgac atcgggaagt tatttccaga tacagaccca   240
gcattcaagg gagctgatag cagagaattg ttacgtgaag catggcgtcg tatacaagca   300
aaaggttaca ctttaggtaa cgtagatgtg acaattattg ctcaggctcc caagatgttg   360
ccccatattc cccagatgcg tgtctttatt gccgaggact tgggttgtca catggatgac   420
gtaaacgtga aggctacgac cactgaaaaa ttgggcttta caggaagggg tgagggtatc   480
gcttgtgaag cagtggcctt gttgatcaag gcaacgaaat taattgagtt tgataatctc   540
acttacctcc acggtaaacc gcaaggcacc gggctgctga aagccaatcc ggaagactt    600 gtggtggtgg aagatttggg cttttgagcct gatggtgaag gtgagcatat tctggttaga   660
atcctcaaaa taaaaaaaaa ggatctcaag aagatccttt gatttt                   706
```